US012649029B2

(12) United States Patent (10) Patent No.: US 12,649,029 B2
DiPierro et al. (45) Date of Patent: Jun. 9, 2026

(54) OPTIMIZED BIO-SYNCHRONOUS BIOACTIVE AGENT DELIVERY SYSTEM

(71) Applicant: Morningside Venture Investments Limited, Newton Centre, MA (US)

(72) Inventors: Guy DiPierro, San Francisco, CA (US); Alan Joel Levy, Bellevue, WA (US)

(73) Assignee: Morningside Venture Investments Limited, Newton Centre, MA (US)

( * ) Notice: Subject to any disclaimer, the term of this patent is extended or adjusted under 35 U.S.C. 154(b) by 660 days.

(21) Appl. No.: 17/936,750

(22) Filed: Sep. 29, 2022

(65) Prior Publication Data

US 2023/0277767 A1 Sep. 7, 2023

Related U.S. Application Data

(60) Continuation of application No. 16/165,720, filed on Oct. 19, 2018, now abandoned, which is a division of (Continued)

(51) Int. Cl.
*A61M 5/172* (2006.01)
*A61M 5/30* (2006.01)
(Continued)

(52) U.S. Cl.
CPC ............ *A61M 5/1723* (2013.01); *A61M 5/30* (2013.01); *G16H 10/20* (2018.01); *G16H 10/60* (2018.01);
(Continued)

(58) Field of Classification Search
None
See application file for complete search history.

(56) References Cited

U.S. PATENT DOCUMENTS 2,183,482 A 12/1939 Kurkjian
3,279,653 A 10/1966 Pfleger
(Continued)

FOREIGN PATENT DOCUMENTS

AU 662877 B3 9/1995
BE 899037 A 6/1984
(Continued)

OTHER PUBLICATIONS

Tong et al.; U.S. Appl. No. 18/665,410 entitled "Drug delivery methods and systems," filed May 15, 2024.
(Continued)

*Primary Examiner* — Manuel A Mendez
(74) *Attorney, Agent, or Firm* — Shay Glenn LLP

(57) ABSTRACT

Optimized bio-synchronous drug delivery begins with establishing a bio-synchronous treatment protocol that incorporates individual temporal and innate biological characteristics into a pharmacological treatment plan. The bio-synchronous treatment protocol is thereafter initiated using bioactive agent delivery device. Bio-synchronous drug delivery includes continual collection of patient data such as physical, psychological, temporal and environmental characteristics. This data is analyzed so to not only determine an initial treatment protocol but to also determining whether modification to the ongoing bio-synchronous treatment protocol is required. And, responsive to determining a modification is required the system modifies the bio-synchronous treatment protocol and use of delivery device. These modifications and treatment protocols can include reactive and proactive psychological support supplied to the patient in a variety of formats.

15 Claims, 6 Drawing Sheets

Related U.S. Application Data application No. 14/156,998, filed on Jan. 16, 2014, now Pat. No. 10,105,487.

(60) Provisional application No. 61/756,339, filed on Jan. 24, 2013.

(51) Int. Cl.

| | |
|---|---|
| *G16H 10/20* | (2018.01) |
| *G16H 10/60* | (2018.01) |
| *G16H 20/17* | (2018.01) |
| *G16H 40/63* | (2018.01) |
| *G16Z 99/00* | (2019.01) |

(52) U.S. Cl.
CPC ............. *G16H 20/17* (2018.01); *G16H 40/63* (2018.01); *G16Z 99/00* (2019.02)

(56) References Cited

U.S. PATENT DOCUMENTS

| | | |
|---|---|---|
| 3,845,217 A | 10/1974 | Ferno et al. |
| 4,313,439 A | 2/1982 | Babb et al. |
| 4,321,387 A | 3/1982 | Chavdarian et al. |
| 4,327,725 A | 5/1982 | Cortese et al. |
| 4,332,945 A | 6/1982 | Edwards |
| 4,379,454 A | 4/1983 | Campbell et al. |
| 4,545,990 A | 10/1985 | Le Foyer de Costil et al. |
| 4,579,858 A | 4/1986 | Femo et al. |
| 4,590,278 A | 5/1986 | Edwards |
| 4,597,961 A | 7/1986 | Etscorn |
| 4,708,716 A | 11/1987 | Sibalis |
| 4,772,263 A | 9/1988 | Dorman et al. |
| 4,806,356 A | 2/1989 | Shaw |
| 4,853,854 A | 8/1989 | Behar et al. |
| 4,885,154 A | 12/1989 | Cormier et al. |
| 4,908,213 A | 3/1990 | Govil et al. |
| 4,917,676 A | 4/1990 | Heiber et al. |
| 4,917,895 A | 4/1990 | Lee et al. |
| 4,920,989 A | 5/1990 | Rose et al. |
| 4,952,928 A | 8/1990 | Carroll et al. |
| 4,953,572 A | 9/1990 | Rose et al. |
| 4,992,445 A | 2/1991 | Lawter et al. |
| 4,994,278 A | 2/1991 | Sablotsky et al. |
| 5,000,956 A | 3/1991 | Amkraut et al. |
| 5,001,139 A | 3/1991 | Lawter et al. |
| 5,013,293 A | 5/1991 | Sibalis |
| 5,023,252 A | 6/1991 | Hseih |
| 5,049,387 A | 9/1991 | Amkraut |
| 5,069,904 A | 12/1991 | Masterson |
| 5,073,380 A | 12/1991 | Babu et al. |
| 5,097,834 A | 3/1992 | Skrabal |
| 5,120,545 A | 6/1992 | Ledger et al. |
| 5,130,139 A | 7/1992 | Cormier et al. |
| 5,149,538 A | 9/1992 | Granger et al. |
| 5,149,719 A | 9/1992 | Ferber et al. |
| 5,212,188 A | 5/1993 | Caldwell et al. |
| 5,221,254 A | 6/1993 | Phipps |
| 5,227,391 A | 7/1993 | Caldwell et al. |
| 5,232,704 A | 8/1993 | Franz et al. |
| 5,232,933 A | 8/1993 | Lippiello et al. |
| 5,236,714 A | 8/1993 | Lee et al. |
| 5,242,934 A | 9/1993 | Lippiello et al. |
| 5,242,935 A | 9/1993 | Lippiello et al. |
| 5,242,941 A | 9/1993 | Lewy et al. |
| 5,248,690 A | 9/1993 | Caldwel et al. |
| 5,252,604 A | 10/1993 | Nagy et al. |
| 5,262,165 A | 11/1993 | Govil et al. |
| 5,273,755 A | 12/1993 | Venkatraman et al. |
| 5,273,756 A | 12/1993 | Fallon et al. |
| 5,304,739 A | 4/1994 | Klug et al. |
| 5,310,404 A | 5/1994 | Gyory et al. |
| 5,352,456 A | 10/1994 | Fallon et al. |
| 5,364,630 A | 11/1994 | Osborne et al. |
| 5,370,635 A | 12/1994 | Strausak et al. |
| 5,388,571 A | 2/1995 | Roberts et al. |
| 5,389,679 A | 2/1995 | Alliger |
| 5,393,526 A | 2/1995 | Castro |
| 5,405,614 A | 4/1995 | D'Angelo et al. |
| 5,415,629 A | 5/1995 | Henley |
| 5,445,609 A | 8/1995 | Lattin et al. |
| 5,451,407 A | 9/1995 | Cormier et al. |
| 5,464,387 A | 11/1995 | Haak et al. |
| 5,472,946 A | 12/1995 | Peck et al. |
| 5,501,697 A | 3/1996 | Fisher |
| 5,505,958 A | 4/1996 | Bello et al. |
| 5,512,306 A | 4/1996 | Carlsson et al. |
| 5,516,793 A | 5/1996 | Duffy |
| 5,525,351 A | 6/1996 | Dam |
| 5,545,407 A | 8/1996 | Hall et al. |
| 5,562,607 A | 10/1996 | Gyory |
| 5,596,994 A | 1/1997 | Bro |
| 5,601,839 A | 2/1997 | Quan et al. |
| 5,616,332 A | 4/1997 | Herstein |
| 5,618,557 A | 4/1997 | Wille et al. |
| 5,653,682 A | 8/1997 | Sibalis |
| 5,656,255 A | 8/1997 | Jones |
| 5,662,920 A | 9/1997 | Santus |
| 5,686,100 A | 11/1997 | Wille et al. |
| 5,688,232 A | 11/1997 | Flower |
| 5,697,896 A | 12/1997 | McNichols et al. |
| 5,716,987 A | 2/1998 | Wille |
| 5,722,418 A | 3/1998 | Bro |
| 5,733,259 A | 3/1998 | Valcke et al. |
| 5,785,688 A | 7/1998 | Joshi et al. |
| 5,797,867 A | 8/1998 | Guerrera et al. |
| 5,820,875 A | 10/1998 | Fallon et al. |
| 5,833,466 A | 11/1998 | Borg |
| 5,843,979 A | 12/1998 | Wille et al. |
| 5,846,559 A | 12/1998 | Hopp |
| 5,865,786 A | 2/1999 | Sibalis et al. |
| 5,876,368 A | 3/1999 | Flower |
| 5,879,292 A | 3/1999 | Sternberg et al. |
| 5,879,322 A | 3/1999 | Lattin et al. |
| 5,882,676 A | 3/1999 | Lee et al. |
| 5,908,301 A | 6/1999 | Lutz |
| 5,919,156 A | 7/1999 | Stropkay et al. |
| 5,932,240 A | 8/1999 | D'Angelo et al. |
| 5,945,123 A | 8/1999 | Hermelin |
| 5,967,789 A | 10/1999 | Segel et al. |
| 5,972,389 A | 10/1999 | Shell et al. |
| 5,993,435 A | 11/1999 | Haak et al. |
| 5,997,501 A | 12/1999 | Gross et al. |
| 6,018,679 A | 1/2000 | Dinh et al. |
| 6,019,997 A | 2/2000 | Scholz et al. |
| 6,024,981 A | 2/2000 | Khankari et al. |
| 6,034,079 A | 3/2000 | Sanberg et al. |
| 6,059,736 A | 5/2000 | Tapper |
| 6,059,753 A | 5/2000 | Faust et al. |
| 6,068,853 A | 5/2000 | Giannos et al. |
| 6,081,734 A | 6/2000 | Batz |
| 6,090,404 A | 7/2000 | Meconi et al. |
| 6,093,419 A | 7/2000 | Rolf |
| 6,120,803 A | 9/2000 | Wong et al. |
| 6,129,702 A | 10/2000 | Woias et al. |
| 6,162,214 A | 12/2000 | Mueller et al. |
| 6,165,155 A | 12/2000 | Jacobsen et al. |
| 6,211,194 B1 | 4/2001 | Westman et al. |
| 6,211,296 B1 | 4/2001 | Frate et al. |
| 6,221,394 B1 | 4/2001 | Gilbert et al. |
| 6,238,689 B1 | 5/2001 | Rhodes et al. |
| 6,274,606 B1 | 8/2001 | Caldwell et al. |
| 6,310,102 B1 | 10/2001 | Dull et al. |
| 6,365,182 B1 | 4/2002 | Khankari et al. |
| 6,368,625 B1 | 4/2002 | Siebert et al. |
| 6,374,136 B1 | 4/2002 | Murdock |
| 6,416,471 B1 | 7/2002 | Kumar et al. |
| 6,417,359 B1 | 7/2002 | Crooks et al. |
| 6,423,747 B1 | 7/2002 | Lanzendörfer et al. |
| 6,436,078 B1 | 8/2002 | Svedman |
| 6,437,004 B1 | 8/2002 | Perricone |
| 6,454,708 B1 | 9/2002 | Ferguson et al. |
| 6,488,959 B2 | 12/2002 | Stanley et al. |
| 6,492,399 B1 | 12/2002 | Dull et al. |

(56)　　　　　　References Cited

U.S. PATENT DOCUMENTS

| | | | |
|---|---|---|---|
| 6,539,250 | B1 | 3/2003 | Bettinger |
| 6,546,281 | B1 | 4/2003 | Zhang et al. |
| 6,567,785 | B2 | 5/2003 | Clendenon |
| 6,569,449 | B1 | 5/2003 | Stinchcomb et al. |
| 6,569,866 | B2 | 5/2003 | Simon |
| 6,576,269 | B1 | 6/2003 | Komneyev |
| 6,579,865 | B2 | 6/2003 | Mak et al. |
| 6,589,229 | B1 | 7/2003 | Connelly et al. |
| 6,595,956 | B1 | 7/2003 | Gross et al. |
| 6,638,528 | B1 | 10/2003 | Kanios |
| 6,638,543 | B2 | 10/2003 | Kang et al. |
| 6,660,295 | B2 | 12/2003 | Watanabe et al. |
| 6,689,380 | B1 | 2/2004 | Marchitto et al. |
| 6,723,086 | B2 | 4/2004 | Bassuk et al. |
| 6,723,340 | B2 | 4/2004 | Gusler et al. |
| 6,746,688 | B1 | 6/2004 | Kushnir et al. |
| 6,791,003 | B1 | 9/2004 | Choi et al. |
| 6,799,576 | B2 | 10/2004 | Farr |
| 6,849,645 | B2 | 2/2005 | Majeed et al. |
| 6,861,066 | B2 | 3/2005 | Van de Casteele |
| 6,867,342 | B2 | 3/2005 | Johnston et al. |
| 6,887,202 | B2 | 5/2005 | Currie et al. |
| 6,893,655 | B2 | 5/2005 | Flanigan et al. |
| 6,900,202 | B2 | 5/2005 | Imoto et al. |
| 6,911,475 | B1 | 6/2005 | Villafane et al. |
| 6,998,176 | B2 | 2/2006 | Morita et al. |
| 7,011,843 | B2 | 3/2006 | Becher et al. |
| 7,011,849 | B2 | 3/2006 | Storm et al. |
| 7,019,622 | B2 | 3/2006 | Orr et al. |
| 7,064,143 | B1 | 6/2006 | Gurley et al. |
| 7,182,955 | B2 | 2/2007 | Hart et al. |
| 7,196,619 | B2 | 3/2007 | Perlman et al. |
| 7,229,641 | B2 | 6/2007 | Cherukuri |
| 7,282,217 | B1 | 10/2007 | Grimshaw et al. |
| 7,332,182 | B2 | 2/2008 | Sackler |
| 7,376,700 | B1 | 5/2008 | Clark et al. |
| 7,384,651 | B2 | 6/2008 | Hille et al. |
| 7,384,653 | B2 | 6/2008 | Wright et al. |
| 7,579,019 | B2 | 8/2009 | Tapolsky et al. |
| 7,598,275 | B2 | 10/2009 | Cooke et al. |
| 7,718,677 | B2 | 5/2010 | Quik et al. |
| 7,780,981 | B2 | 8/2010 | DiPierro et al. |
| 7,931,563 | B2 | 4/2011 | Shaw et al. |
| 7,988,660 | B2 | 8/2011 | Byland et al. |
| 8,003,080 | B2 | 8/2011 | Rabinowitz et al. |
| 8,021,334 | B2 | 9/2011 | Shekalim |
| 8,137,314 | B2 | 3/2012 | Mounce et al. |
| 8,140,143 | B2 | 3/2012 | Picard et al. |
| 8,192,756 | B2 | 6/2012 | Berner et al. |
| 8,246,581 | B2 | 8/2012 | Adams et al. |
| 8,252,321 | B2 | 8/2012 | DiPierro et al. |
| 8,262,394 | B2 | 9/2012 | Walker et al. |
| 8,268,475 | B2 | 9/2012 | Tucholski |
| 8,285,328 | B2 | 10/2012 | Caffey et al. |
| 8,303,500 | B2 | 11/2012 | Raheman |
| 8,309,568 | B2 | 11/2012 | Stinchcomb et al. |
| 8,372,040 | B2 | 2/2013 | Huang et al. |
| 8,414,532 | B2 | 4/2013 | Brandt et al. |
| 8,440,220 | B2 | 5/2013 | Gale et al. |
| 8,440,221 | B2 | 5/2013 | Zumbrunn et al. |
| 8,441,411 | B2 | 5/2013 | Tucholski et al. |
| 8,445,010 | B2 | 5/2013 | Anderson et al. |
| 8,449,471 | B2 | 5/2013 | Tran |
| 8,517,988 | B2 | 8/2013 | Smith |
| 8,545,445 | B2 | 10/2013 | Kamen et al. |
| 8,574,188 | B2 | 11/2013 | Potter et al. |
| 8,586,079 | B2 | 11/2013 | Hansted et al. |
| 8,589,174 | B2 | 11/2013 | Nelson et al. |
| 8,614,278 | B2 | 12/2013 | Loubert et al. |
| 8,632,497 | B2 | 1/2014 | Yodfat et al. |
| 8,666,781 | B2 | 3/2014 | Hanina et al. |
| 8,673,346 | B2 | 3/2014 | Zumbrunn et al. |
| 8,684,922 | B2 | 4/2014 | Tran |
| 8,688,189 | B2 | 4/2014 | Shennib |
| 8,690,827 | B2 | 4/2014 | Edwards et al. |
| 8,690,865 | B2 | 4/2014 | Prausnitz et al. |
| 8,696,637 | B2 | 4/2014 | Ross |
| 8,703,175 | B2 | 4/2014 | Kanios et al. |
| 8,703,177 | B2 | 4/2014 | Finn et al. |
| 8,722,233 | B2 | 5/2014 | Tucholski |
| 8,727,745 | B2 | 5/2014 | Rush et al. |
| 8,741,336 | B2 | 6/2014 | DiPierro et al. |
| 8,747,348 | B2 | 6/2014 | Yodfat et al. |
| 8,753,315 | B2 | 6/2014 | Alferness et al. |
| 8,773,257 | B2 | 7/2014 | Yodfat et al. |
| 8,814,822 | B2 | 8/2014 | Yodfat et al. |
| 8,862,223 | B2 | 10/2014 | Yanaki |
| 8,864,727 | B2 | 10/2014 | Lee |
| 8,865,207 | B2 | 10/2014 | Kanios et al. |
| 8,872,663 | B2 | 10/2014 | Forster |
| 8,876,802 | B2 | 11/2014 | Grigorov |
| 8,956,644 | B2 | 2/2015 | Yum et al. |
| 8,962,014 | B2 | 2/2015 | Prinz et al. |
| 8,986,253 | B2 | 3/2015 | DiPerna |
| 8,999,356 | B1 | 4/2015 | Ramirez et al. |
| 8,999,372 | B2 | 4/2015 | Davidson et al. |
| 9,023,392 | B2 | 5/2015 | Koo et al. |
| 9,044,582 | B2 | 6/2015 | Chang et al. |
| 9,050,348 | B2 | 6/2015 | Kydonieus et al. |
| 9,078,833 | B2 | 7/2015 | Audett |
| 9,111,085 | B1 | 8/2015 | Darmour et al. |
| 9,114,240 | B2 | 8/2015 | Horstmann et al. |
| 9,155,712 | B2 | 10/2015 | Kanios et al. |
| 9,233,203 | B2 | 1/2016 | Moberg et al. |
| 9,238,001 | B2 | 1/2016 | Weyer et al. |
| 9,238,108 | B2 | 1/2016 | Edwards et al. |
| 9,248,104 | B2 | 2/2016 | Valia et al. |
| 9,289,397 | B2 | 3/2016 | Wright |
| 9,308,202 | B2 | 4/2016 | Hille et al. |
| 9,314,527 | B2 | 4/2016 | Cottrell et al. |
| 9,373,269 | B2 | 6/2016 | Bergman et al. |
| RE46,217 | E | 11/2016 | Huang et al. |
| 9,549,903 | B2 | 1/2017 | Hille et al. |
| 9,555,226 | B2 | 1/2017 | Zumbrunn et al. |
| 9,555,227 | B2 | 1/2017 | Dipierro |
| 9,555,277 | B2 | 1/2017 | Yeh |
| 9,655,843 | B2 | 5/2017 | Finn et al. |
| 9,669,199 | B2 | 6/2017 | DiPierro et al. |
| 9,687,186 | B2 | 6/2017 | Goldstein et al. |
| 9,700,552 | B2 | 7/2017 | Weimann |
| 9,717,698 | B2 | 8/2017 | Horstmann et al. |
| 9,782,082 | B2 | 10/2017 | Gannon et al. |
| 9,795,681 | B2 | 10/2017 | Abreu |
| 9,895,320 | B2 | 2/2018 | Ogino et al. |
| 10,004,447 | B2 | 6/2018 | Shen et al. |
| 10,034,841 | B2 | 7/2018 | Müller et al. |
| 10,105,487 | B2 | 10/2018 | DiPierro et al. |
| 10,213,586 | B2 | 2/2019 | Netzel et al. |
| 10,232,156 | B2 | 3/2019 | Netzel et al. |
| 10,258,738 | B2 | 4/2019 | Dipierro et al. |
| 10,258,778 | B2 | 4/2019 | Dipierro et al. |
| 10,679,516 | B2 | 6/2020 | Darmour et al. |
| 10,716,764 | B2 | 7/2020 | Zumbrunn et al. |
| 11,285,306 | B2 | 3/2022 | Johnson et al. |
| 11,400,266 | B2 | 8/2022 | Netzel et al. |
| 11,471,424 | B2 | 10/2022 | DiPierro |
| 11,596,779 | B2 | 3/2023 | Tong et al. |
| 2001/0022978 | A1 | 9/2001 | Lacharriere et al. |
| 2001/0026788 | A1 | 10/2001 | Piskorz |
| 2002/0002189 | A1 | 1/2002 | Smith et al. |
| 2002/0034535 | A1 | 3/2002 | Kleiner et al. |
| 2002/0106329 | A1 | 8/2002 | Leslie |
| 2002/0127256 | A1 | 9/2002 | Murad |
| 2002/0165170 | A1 | 11/2002 | Wilson et al. |
| 2002/0169439 | A1 | 11/2002 | Flaherty |
| 2002/0182238 | A1 | 12/2002 | Creton |
| 2003/0004187 | A1 | 1/2003 | Bedard et al. |
| 2003/0065294 | A1 | 4/2003 | Pickup et al. |
| 2003/0065924 | A1 | 4/2003 | Wuldart et al. |
| 2003/0083645 | A1 | 5/2003 | Angel et al. |
| 2003/0087937 | A1 | 5/2003 | Lindberg |
| 2003/0119879 | A1 | 6/2003 | Landh et al. |
| 2003/0138464 | A1 | 7/2003 | Zhang et al. |
| 2003/0159702 | A1 | 8/2003 | Lindell et al. |

(56) References Cited

U.S. PATENT DOCUMENTS

| | | |
|---|---|---|
| 2004/0019321 A1 | 1/2004 | Sage et al. |
| 2004/0034068 A1 | 2/2004 | Warchol et al. |
| 2004/0037879 A1 | 2/2004 | Adusumilli et al. |
| 2004/0052843 A1 | 3/2004 | Lerner et al. |
| 2004/0062802 A1 | 4/2004 | Hermelin |
| 2004/0138074 A1 | 7/2004 | Ahmad et al. |
| 2004/0166159 A1 | 8/2004 | Han et al. |
| 2004/0191322 A1 | 9/2004 | Hansson |
| 2004/0194793 A1 | 10/2004 | Lindell et al. |
| 2004/0219192 A1 | 11/2004 | Horstmann et al. |
| 2004/0229908 A1 | 11/2004 | Nelson |
| 2004/0241218 A1 | 12/2004 | Tavares et al. |
| 2004/0253249 A1 | 12/2004 | Rudnic et al. |
| 2004/0259816 A1 | 12/2004 | Pandol et al. |
| 2005/0002806 A1 | 1/2005 | Fuechslin et al. |
| 2005/0014779 A1 | 1/2005 | Papke |
| 2005/0021092 A1 | 1/2005 | Yun et al. |
| 2005/0034842 A1 | 2/2005 | Huber et al. |
| 2005/0048020 A1 | 3/2005 | Wille |
| 2005/0053665 A1 | 3/2005 | Ek et al. |
| 2005/0113452 A1 | 5/2005 | Flashner Barak et al. |
| 2005/0141346 A1 | 6/2005 | Rawls et al. |
| 2005/0151110 A1 | 7/2005 | Minor et al. |
| 2005/0159419 A1 | 7/2005 | Stephenson et al. |
| 2005/0197625 A1 | 9/2005 | Haueter et al. |
| 2005/0266032 A1 | 12/2005 | Srinivasan et al. |
| 2005/0276852 A1 | 12/2005 | Davis et al. |
| 2006/0024358 A1 | 2/2006 | Santini et al. |
| 2006/0036209 A1 | 2/2006 | Subramony et al. |
| 2006/0057202 A1 | 3/2006 | Antarkar et al. |
| 2006/0122577 A1 | 6/2006 | Poulsen et al. |
| 2006/0135911 A1 | 6/2006 | Mittur |
| 2006/0167039 A1 | 7/2006 | Nguyen et al. |
| 2006/0173439 A1 | 8/2006 | Thorne et al. |
| 2006/0184093 A1 | 8/2006 | Phipps et al. |
| 2006/0188859 A1 | 8/2006 | Yakobi |
| 2006/0204578 A1 | 9/2006 | Vergez et al. |
| 2006/0206054 A1 | 9/2006 | Shekalim |
| 2007/0026054 A1 | 2/2007 | Theobald et al. |
| 2007/0042026 A1 | 2/2007 | Wille |
| 2007/0065365 A1 | 3/2007 | Kugelmann et al. |
| 2007/0086275 A1 | 4/2007 | Robinson et al. |
| 2007/0088338 A1 | 4/2007 | Ehwald et al. |
| 2007/0104787 A1 | 5/2007 | Posey Dowty et al. |
| 2007/0149952 A1 | 6/2007 | Bland et al. |
| 2007/0154336 A1 | 7/2007 | Miyazaki et al. |
| 2007/0168501 A1 | 7/2007 | Cobb et al. |
| 2007/0179172 A1 | 8/2007 | Becker et al. |
| 2007/0191815 A1* | 8/2007 | DiPierro ............... A61M 39/22 |
| | | 604/890.1 |
| 2007/0250018 A1 | 10/2007 | Adachi et al. |
| 2007/0255195 A1 | 11/2007 | Adachi |
| 2007/0256684 A1 | 11/2007 | Kelliher et al. |
| 2007/0260491 A1 | 11/2007 | Palmer et al. |
| 2007/0279217 A1 | 12/2007 | Venkatraman et al. |
| 2007/0299401 A1 | 12/2007 | Alferness et al. |
| 2008/0008747 A1 | 1/2008 | Royds |
| 2008/0015494 A1 | 1/2008 | Santini, Jr. et al. |
| 2008/0131494 A1 | 6/2008 | Reed et al. |
| 2008/0138294 A1 | 6/2008 | Gonda |
| 2008/0138398 A1 | 6/2008 | Gonda |
| 2008/0138399 A1 | 6/2008 | Gonda |
| 2008/0138423 A1 | 6/2008 | Gonda |
| 2008/0139907 A1* | 6/2008 | Rao ...................... A61B 5/1171 |
| | | 600/323 |
| 2008/0152592 A1 | 6/2008 | Rebec |
| 2008/0195946 A1 | 8/2008 | Peri-Glass |
| 2008/0201174 A1 | 8/2008 | Ramasubramanian et al. |
| 2008/0220092 A1* | 9/2008 | Dipierro .................. A61N 1/30 |
| | | 514/249 |
| 2008/0233178 A1 | 9/2008 | Reidenberg et al. |
| 2008/0274168 A1 | 11/2008 | Baker et al. |
| 2008/0319272 A1* | 12/2008 | Patangay .................. A61B 5/74 |
| | | 600/300 |
| 2009/0005009 A1 | 1/2009 | Marsili |
| 2009/0010998 A1 | 1/2009 | Marchitto et al. |
| 2009/0024004 A1 | 1/2009 | Yang |
| 2009/0028824 A1 | 1/2009 | Chiang et al. |
| 2009/0048563 A1 | 2/2009 | Ethelfeld et al. |
| 2009/0062754 A1 | 3/2009 | Tang |
| 2009/0118710 A1 | 5/2009 | Kortzeborn |
| 2009/0169631 A1 | 7/2009 | Zamloot et al. |
| 2009/0246265 A1 | 10/2009 | Stinchcomb et al. |
| 2009/0247985 A1 | 10/2009 | Melsheimer et al. |
| 2009/0259176 A1 | 10/2009 | Yairi |
| 2009/0299156 A1* | 12/2009 | Simpson .............. A61B 5/0002 |
| | | 600/301 |
| 2010/0003653 A1 | 1/2010 | Brown |
| 2010/0010443 A1 | 1/2010 | Morgan et al. |
| 2010/0068250 A1 | 3/2010 | Anderson et al. |
| 2010/0114008 A1 | 5/2010 | Marchitto et al. |
| 2010/0130932 A1 | 5/2010 | Yodfat et al. |
| 2010/0145303 A1 | 6/2010 | Yodfat et al. |
| 2010/0179473 A1 | 7/2010 | Genosar |
| 2010/0196463 A1 | 8/2010 | Quik et al. |
| 2010/0198187 A1 | 8/2010 | Yodfat et al. |
| 2010/0211005 A1 | 8/2010 | Edwards et al. |
| 2010/0248198 A1 | 9/2010 | Seidman et al. |
| 2010/0273738 A1 | 10/2010 | Valcke et al. |
| 2010/0280432 A1 | 11/2010 | DiPierro et al. |
| 2011/0004072 A1 | 1/2011 | Fletcher et al. |
| 2011/0053129 A1 | 3/2011 | Basson et al. |
| 2011/0054285 A1 | 3/2011 | Searle et al. |
| 2011/0109439 A1 | 5/2011 | Borlenghi |
| 2011/0137255 A1 | 6/2011 | Nielsen et al. |
| 2011/0152635 A1 | 6/2011 | Morris et al. |
| 2011/0153360 A1 | 6/2011 | Hanina et al. |
| 2011/0160640 A1 | 6/2011 | Yanaki |
| 2011/0160655 A1 | 6/2011 | Hanson et al. |
| 2011/0212027 A1 | 9/2011 | Hoare et al. |
| 2011/0241446 A1 | 10/2011 | Tucholski |
| 2011/0245633 A1 | 10/2011 | Goldberg et al. |
| 2011/0245783 A1 | 10/2011 | Stinchcomb et al. |
| 2011/0250576 A1 | 10/2011 | Hester |
| 2011/0256517 A1 | 10/2011 | Swanson |
| 2011/0264028 A1 | 10/2011 | Ramdas et al. |
| 2011/0268809 A1 | 11/2011 | Brinkley et al. |
| 2011/0275987 A1 | 11/2011 | Caffey et al. |
| 2012/0046644 A1 | 2/2012 | Ziaie et al. |
| 2012/0078216 A1 | 3/2012 | Smith et al. |
| 2012/0123387 A1 | 5/2012 | Gonzalez et al. |
| 2012/0156138 A1 | 6/2012 | Smith |
| 2012/0171277 A1 | 7/2012 | Royds |
| 2012/0178065 A1 | 7/2012 | Naghavi et al. |
| 2012/0191043 A1 | 7/2012 | Yodfat et al. |
| 2012/0203573 A1 | 8/2012 | Mayer et al. |
| 2012/0209223 A1 | 8/2012 | Salman et al. |
| 2012/0221251 A1 | 8/2012 | Rosenberg et al. |
| 2012/0244503 A1 | 9/2012 | Neveldine |
| 2012/0302844 A1 | 11/2012 | Schnidrig et al. |
| 2012/0316896 A1 | 12/2012 | Rahman et al. |
| 2012/0329017 A1 | 12/2012 | Pham |
| 2013/0017259 A1 | 1/2013 | Azhir |
| 2013/0041258 A1 | 2/2013 | Patrick et al. |
| 2013/0096495 A1 | 4/2013 | Holmqvist et al. |
| 2013/0123719 A1 | 5/2013 | Mao et al. |
| 2013/0158430 A1 | 6/2013 | Aceti et al. |
| 2013/0178826 A1 | 7/2013 | Li |
| 2013/0190683 A1 | 7/2013 | Hanson et al. |
| 2013/0216989 A1 | 8/2013 | Cuthbert |
| 2013/0253430 A1 | 9/2013 | Kouyoumjian et al. |
| 2013/0302398 A1 | 11/2013 | Ambati et al. |
| 2013/0311917 A1 | 11/2013 | Bar-or et al. |
| 2013/0317384 A1 | 11/2013 | Le |
| 2013/0328572 A1 | 12/2013 | Wang et al. |
| 2013/0345633 A1 | 12/2013 | Chong |
| 2014/0039396 A1 | 2/2014 | Geipel et al. |
| 2014/0046288 A1 | 2/2014 | Geipel et al. |
| 2014/0073883 A1 | 3/2014 | Rao et al. |
| 2014/0088554 A1 | 3/2014 | Li et al. |
| 2014/0099614 A1 | 4/2014 | Hu et al. |
| 2014/0100241 A1 | 4/2014 | Slater et al. |
| 2014/0163521 A1 | 6/2014 | O'Conner |
| 2014/0200525 A1 | 7/2014 | DiPierro |

(56) References Cited

U.S. PATENT DOCUMENTS

| | | |
|---|---|---|
| 2014/0206327 A1 | 7/2014 | Ziemianska et al. |
| 2014/0207047 A1 | 7/2014 | DiPierro et al. |
| 2014/0228736 A1 | 8/2014 | Eppstein et al. |
| 2014/0237028 A1 | 8/2014 | Messenger et al. |
| 2014/0240124 A1 | 8/2014 | Bychkov |
| 2014/0266584 A1 | 9/2014 | Ingle et al. |
| 2014/0272844 A1 | 9/2014 | Hendriks et al. |
| 2014/0272845 A1 | 9/2014 | Hendriks et al. |
| 2014/0272846 A1 | 9/2014 | Richling |
| 2014/0275135 A1 | 9/2014 | Genov et al. |
| 2014/0275932 A1 | 9/2014 | Zadig |
| 2014/0276127 A1 | 9/2014 | Ferdosi et al. |
| 2014/0279740 A1 | 9/2014 | Wernevi et al. |
| 2014/0302121 A1 | 10/2014 | Bevier |
| 2014/0303574 A1 | 10/2014 | Knutson |
| 2014/0365408 A1 | 12/2014 | Snyder et al. |
| 2014/0378943 A1 | 12/2014 | Geipel |
| 2015/0057616 A1 | 2/2015 | Shergold et al. |
| 2015/0209783 A1 | 7/2015 | Ingber et al. |
| 2015/0273148 A1 | 10/2015 | Sexton et al. |
| 2016/0030412 A1 | 2/2016 | Azhir |
| 2016/0220553 A1 | 8/2016 | Azhir |
| 2016/0227361 A1 | 8/2016 | Booth et al. |
| 2016/0235732 A1 | 8/2016 | Quik et al. |
| 2016/0235916 A1 | 8/2016 | Edwards et al. |
| 2016/0310664 A1 | 10/2016 | McKenzie et al. |
| 2016/0317738 A1 | 11/2016 | Cross et al. |
| 2017/0100573 A1 | 4/2017 | DiPierro |
| 2017/0207825 A1 | 7/2017 | Belogolovy |
| 2017/0296317 A1 | 10/2017 | Gordon |
| 2018/0110768 A1 | 4/2018 | Quik et al. |
| 2018/0374381 A1 | 12/2018 | Darmour et al. |
| 2019/0054078 A1 | 2/2019 | Azhir et al. |
| 2019/0054235 A1 | 2/2019 | DiPierro et al. |
| 2019/0231707 A1 | 8/2019 | Stiles et al. |
| 2019/0374482 A1 | 12/2019 | Schaller et al. |
| 2020/0030590 A1 | 1/2020 | Buchman et al. |
| 2020/0368175 A1 | 11/2020 | Arora et al. |
| 2021/0169822 A1 | 6/2021 | Zumbrunn et al. |
| 2021/0196935 A1 | 7/2021 | Tong et al. |
| 2022/0001158 A1 | 1/2022 | Ruane et al. |
| 2022/0280763 A1 | 9/2022 | Johnston et al. |
| 2024/0408362 A1 | 12/2024 | Johnston et al. |

FOREIGN PATENT DOCUMENTS

| | | |
|---|---|---|
| CA | 2142871 A1 | 3/1994 |
| CN | 1704056 A | 12/2005 |
| DE | 19958554 A1 | 1/2001 |
| DE | 10105759 C1 | 10/2001 |
| DE | 10103158 A1 | 8/2002 |
| EP | 311313 A2 | 4/1989 |
| EP | 0314528 B1 | 12/1992 |
| EP | 0354554 B1 | 1/1994 |
| EP | 0726005 A1 | 8/1996 |
| EP | 857725 A1 | 8/1998 |
| EP | 870768 A1 | 10/1998 |
| EP | 955301 A2 | 11/1999 |
| EP | 0612525 B1 | 9/2001 |
| EP | 1815784 A1 | 8/2007 |
| EP | 1977746 B1 | 7/2014 |
| EP | 1662989 B1 | 9/2014 |
| EP | 3016586 A2 | 5/2016 |
| GB | 1528391 A | 10/1978 |
| GB | 2030862 A | 4/1980 |
| GB | 2142822 A | 1/1985 |
| GB | 2230439 A | 10/1990 |
| JP | 02202813 A | 8/1990 |
| JP | H09504974 A | 5/1997 |
| JP | 09512006 A | 12/1997 |
| JP | 2000515394 A | 11/2000 |
| JP | 2001505491 A | 4/2001 |
| JP | 2002092180 A | 3/2002 |
| JP | 2003506477 A | 2/2003 |
| JP | 2005521526 A | 7/2005 |
| JP | 2005525147 A | 8/2005 |
| JP | 2007509661 A | 4/2007 |
| JP | 2008523918 A | 7/2008 |
| JP | 2009544338 A | 12/2009 |
| JP | 2010/507457 | 3/2010 |
| JP | 2010518914 A | 6/2010 |
| JP | 2010279808 A | 12/2010 |
| JP | 2011036491 A | 2/2011 |
| JP | 2013524951 A | 6/2013 |
| JP | 2015070868 A | 4/2015 |
| WO | WO86/07269 A1 | 12/1986 |
| WO | WO88/003803 A1 | 6/1988 |
| WO | WO91/14441 A1 | 10/1991 |
| WO | WO92/021339 A1 | 12/1992 |
| WO | WO94/008992 A1 | 4/1994 |
| WO | WO94/010987 A1 | 5/1994 |
| WO | WO95/06497 A1 | 3/1995 |
| WO | WO96/015123 A1 | 5/1996 |
| WO | WO96/040682 A1 | 12/1996 |
| WO | WO97/011072 A1 | 3/1997 |
| WO | WO97/011073 A1 | 3/1997 |
| WO | WO97/11741 A1 | 4/1997 |
| WO | WO97/18782 A1 | 5/1997 |
| WO | WO97/019059 A1 | 5/1997 |
| WO | WO97/028801 A1 | 8/1997 |
| WO | WO97/034605 A1 | 9/1997 |
| WO | WO97/042941 A2 | 11/1997 |
| WO | WO97/046554 A1 | 12/1997 |
| WO | WO98/042713 A1 | 10/1998 |
| WO | WO98/46093 A1 | 10/1998 |
| WO | WO98/054152 A1 | 12/1998 |
| WO | WO98/054181 A1 | 12/1998 |
| WO | WO98/054182 A1 | 12/1998 |
| WO | WO98/054189 A1 | 12/1998 |
| WO | WO98/55107 A1 | 12/1998 |
| WO | WO99/002517 A1 | 1/1999 |
| WO | WO99/003859 A1 | 1/1999 |
| WO | WO99/021834 A1 | 5/1999 |
| WO | WO99/024422 A1 | 5/1999 |
| WO | WO99/066916 A1 | 12/1999 |
| WO | WO00/010997 A1 | 3/2000 |
| WO | WO00/032600 A1 | 6/2000 |
| WO | WO00/034279 A1 | 6/2000 |
| WO | WO00/034284 A1 | 6/2000 |
| WO | WO00/035279 A1 | 6/2000 |
| WO | WO00/035456 A1 | 6/2000 |
| WO | WO00/044755 A1 | 8/2000 |
| WO | WO00/064885 A1 | 11/2000 |
| WO | WO00/066596 A1 | 11/2000 |
| WO | WO00/74763 A2 | 12/2000 |
| WO | WO00/74933 A1 | 12/2000 |
| WO | WO01/005459 A1 | 1/2001 |
| WO | WO01/037814 A1 | 5/2001 |
| WO | WO02/076211 A1 | 10/2002 |
| WO | WO03/022349 A2 | 3/2003 |
| WO | WO03/026655 A1 | 4/2003 |
| WO | WO03/055486 A1 | 7/2003 |
| WO | WO03/061656 A1 | 7/2003 |
| WO | WO03/070191 A1 | 8/2003 |
| WO | WO03/097146 A1 | 11/2003 |
| WO | WO2004/024124 A1 | 3/2004 |
| WO | WO2004/073429 A1 | 9/2004 |
| WO | WO2005/023227 A2 | 3/2005 |
| WO | WO2005/079161 A2 | 9/2005 |
| WO | WO2006/069097 A2 | 6/2006 |
| WO | WO2007/013975 A2 | 2/2007 |
| WO | WO2007/041544 A2 | 4/2007 |
| WO | WO2007/104574 A2 | 9/2007 |
| WO | WO2007/104575 A2 | 9/2007 |
| WO | WO2007/133141 A1 | 11/2007 |
| WO | WO2008/024408 A2 | 2/2008 |
| WO | WO2008/054788 A2 | 5/2008 |
| WO | WO2008/069921 A2 | 6/2008 |
| WO | WO2008/069970 A2 | 6/2008 |
| WO | WO2008/069972 A2 | 6/2008 |
| WO | WO2008/122049 A2 | 10/2008 |
| WO | WO2008/135283 A1 | 11/2008 |
| WO | WO2009/136304 A2 | 11/2009 |
| WO | WO2011/088072 A2 | 7/2011 |

(56) References Cited

FOREIGN PATENT DOCUMENTS

| WO | WO2012/012846 A1 | 2/2012 |
| WO | WO2012/101060 A1 | 8/2012 |
| WO | WO2013/093666 A1 | 6/2013 |
| WO | WO2013/168068 A1 | 11/2013 |
| WO | WO2014/001877 A1 | 1/2014 |
| WO | WO2014/043502 A1 | 3/2014 |
| WO | WO2015/094945 A1 | 6/2015 |

OTHER PUBLICATIONS

Netzel et al.; U.S. Appl. No. 18/673,223 entitled "Drug delivery methods and systems," filed May 23, 2024.

Tong et al.; U.S. Appl. No. 18/178,442 entitled "Drug Delivery methods and systems," filed Mar. 3, 2023.

Abood et al.; Structure-activity studies of carbamate and other esters: agonists and antagonists to nicotine; Pharmacology Biochemistry and Behavior; 30(2); pp. 403-408; Jun. 1988.

Ahlskog et al.; Frequency of levodopa-related dyskinesias and motor fluctuations as estimated from the cumulative literature; Movement Disorders; 16(3); pp. 448-458; May 1, 2001.

Angulo et al.; Oral nicotine in treatment of primary sclerosing cholangitis: a pilot study; Digestive diseases and sciences; 44(3); pp. 602-607; Mar. 1, 1999.

Baldessarini et al.; Preclinical studies of the pharmacology of aporphines; in: Gessa GL, Corsini GU, eds.; Apomorphine and other dopaminomi-metics vol. 1, Basic pharmacology; New York: Raven Press; pp. 219-228; (the year of publication is sufficiently earlier than the effective U.S. filing date and any foreign priority date so that the particular month of publication is not in issue) 1981.

Balfour et al.; Pharmacology of nicotine and its therapeutic use in smoking cessation and neurodegenerative disorders; Pharmacology and Therapeutics; 72(1); pp. 51-81; Jan. 1, 1996.

Benowitz et al.; Sources of variability in nicotine and cotinine levels with use of nicotine nasal spray, transdermal nicotine, and cigarette smoking; British Journal of Clinical Pharmacology: 43(3); pp. 259-267; Mar. 1, 1997.

Benowitz et al.; Stable isotope studies of nicotine kinetics and bioavailability; Clin Pharm and Ther; 49(3); pp. 270-277; Mar. 1991.

Bordia et al.; Continuous and intermittent nicotine treatment reduces L-3 4-dihydroxyphenyalanine (L-DOPA)-induced dyskinesias in rat model of Parkinson's diseases; Journal of Pharmacology ans Experimental Therapeutics; 327(1); pp. 239-247; Oct. 1, 2008.

Bordia et al.; Partial recovery of striatal nicotinic receptors in I-methyl-4-phenyl-1,2,3,6-tetrahydropyridine (MPTP)-lesioned monkeys with chronic oral nicotinic; The Journal of Pharmacology and Experimental Therapeutics; 319(1); pp. 285-292; Oct. 1, 2006.

Bove et al.; Toxin-induced models of Parkinson's disease; NeuroRx; 2(3); pp. 484-494; Jul. 31, 2005.

Brotchie et al.; Levodopa-induced dyskinesia in Parkinson's disease; Journal of Neural Transmission; 112(3); pp. 359-391; Mar. 1, 2005.

Bruguerolle; Chronopharmacokinetics; Clin Pharmacokinet; 35(2); pp. 83-94; Aug. 1998.

Calabresi et al.; Levodopa-induced dyskinesias inpatients with parkinson's disease: filling the bench-to-bedside gap; The Lancet Neurology; 9(11); pp. 1106-1117; Nov. 1, 2010.

Carta et al.; Role of striatal L-DOPA in the production of dyskinesia in 6-hydroxydopamine lesioned rats; Journal of Neurochemistry; 96(6); pp. 1718-1727; Mar. 2006.

Chen et al.; Enhanced striatal opioid receptor-mediated G-protein activation in L-DOPA-treated dyskinetic monkeys; Neuroscience; 132(2); pp. 409-420; Dec. 31, 2005.

Damaj et al.; Antinociceptive responses to nicotinic acetylcholine receptor ligands after systemic and intrathecal administration in mice; Journal of Pharmacology and Experimental Therapeutics; 284(3); pp. 1058-1065; Mar. 1, 1998.

Davie; A review of Parkinson's disease. British Medical Bulletin 2008 86(1): 109-127; Apr. 8, 2008.

De La Fuente et al.; The placebo effect in Parkinson's disease; Trends in Neuroscience; 25(6); pp. 302-306; Jun. 1, 2002.

Di Monte et al.; Relationship among nigrostriatal denervation, parkinsonism, and dyskinesias in the MPTP primate model; Movement Disorders; 15(3); pp. 459-466; May 1, 2000.

Dockser-Marcus, A.; New research shows drugs work best at certain times; The Wall Street Journal; 6 pgs.; May 27, 2003; (http://www.wsj.com/articles/SB105397312486508700).

Domino et al.; Nicotine alone and in combination with L-DOPA methyl ester or the D(2) agonist N-0923 in MPTP-induced chronic hemiparkinsonian monkeys; Exp Neurol; 158(2); pp. 414-421; Aug. 1999.

Dutil; Benzoyl Peroxide: Enhancing antibiotic efficacy in acne management; Skin Therapy Letter; 15(1); pp. 5-7; Nov./Dec. 2010.

Ebersbach et al.; Worsening of motor performance in patients with Parkinson's disease following transdermal nicotine administration; Movement Disorders; 14(6); pp. 1011-1013; Nov. 1, 1999.

Ethicon Endo-Surgery, Inc.; Sedasys® Computer-assisted personalized sedation system essential product information; retrieved May 12, 2015 from the internet (http://www.sedasys.com/explore-the-system/essential-product-information); 2 pgs.

Fagerstrom et al.; Nicotine may relieve symptoms of Parkinson's disease; Psychopharmacology; 116(1); pp. 117-119; Sep. 16, 1994.

Food and Drug Administration; Guidance for Industry—Dissolution Testing of Immediate Release Solid Oral Dosage Forms; 17 pages; retrieved from the internet (https://www.fda.gov/downloads/drugs/guidances/ucm070237.pdf); Aug. 1997.

Gatto et al.; TC-1734: An orally active neuronal nicotinic acetylcholine receptor modulator with antidepressant, neuroprotective and long-lasting cognitive effects; CNS Drug Reviews; 10(2); pp. 147-166; Jun. 1, 2004.

Gennaro (Editor); Remington: The Science and Practice of Pharmacy; 19th Ed.; Mack Publishing Co.; Easton, PA; p. 1582-1584; Jun. 1995.

Giannos; Chapter 20: Pulsatile fSmartf Drug Delivery, in Skin Delivery Systems: Transdermals, Dermatologicals, and Cosmetic Actives; (ed.) Wille, Jr; Blackwell Pub.; Oxford, UK; pp. 327-357; Jun. 2006.

Gora; Nicotine transdermal systems; The Annals of Pharmacotherapy; 27(6); pp. 742-750; Jun. 1993.

Gotti et al.; Brain nicotinic acetylcholine receptors: native subtypes and their relevance; Treands in Pharmacological Sciences; 27(9); pp. 482-491; Sep. 30, 2006.

Green et al.; An oral formulation of nicotine for release and absorption in the colon: its development and pharmacokinetics. British Journal of Clinical Pharmacology; 48(4); pp. 485-493; Oct. 1999.

Gries et al.; Importance of Chronopharmacokinetics in Design and Evaluation of Transdermal Drug Delivery Systems; J Pharmacol Exp Ther; 285(2); pp. 457-463; May 1998.

Guy; Current status and future prospects of transdermal drug delivery; Pharm Res; 13(12); pp. 1765-1769; Dec. 1996.

Halberg et al.; Chronomics: circadian and circaseptan timing of radiotherapy, drugs, calories, perhaps nutriceuticals and beyond; Journal of Experimental Therapeutics and Oncology; 3(5); pp. 223-260; Sep. 2003.

He et al.; Autoradiographic analysis of dopamine receptor-stimulated [35S]GTPtS binding in rat striatum; Brain Research; 885(1); pp. 133-136; Dec. 1, 2000.

He et al; Autoradiographic analysis of N-methyl-D-aspartate receptor binding in monkey brain: Effects of I-methyl-4-phenyl-1,2,3,6-tetrahydropyridine andlevodopa treatment; Neuroscience; 99(4); pp. 697-704; Aug. 23, 2000.

Hrushesky; Temporally optimizable delivery systems: sine qua non for the next therapeutic revolution; J Cont Rel; 19(1-3); pp. 363-368; Mar. 1992.

Hsu et al.; Effect of the D3 dopamine receptor partial agonist BP897 [N-[4-(4-(2-methoxyphenyl)piperazinyl) butyl]-2-napthamide] on L-3,4-dihydroxyphenylalanine-induced dyskinesias and parkinsonism in squirrel monkeys; The Journal of Pharmacology and Experimental Therapeutics. 311(2); pp. 770-777; Nov. 1, 2004.

(56)　　　　　　References Cited

OTHER PUBLICATIONS

Huang et al.; Inhibitory effects of curcumin on in vitro lipoxygenase and cyclooxygenase activities in mouse epidermis; Cancer Res; 51(3); pp. 813-819; Feb. 1991.

Hukkanen et al., Metabolism and disposition kinetics of nicotine; Pharmacological Reviews; 57(1); pp. 79-115; Mar. 1, 2005.

Hurley; Growing list of positive effects of nicotine seen in neurodegenerative disorders; Neurology Today; 12(2); pp. 37-38; Jan. 19, 2012.

Ingram et al.; Preliminary observations of oral nicotine therapy for inflammatory bowel disease: an open-label phase I-II study of tolerance; Inflamm Bowel Diseases; 11(12); pp. 1092-1096; Dec. 1, 2005.

Janson et al.; Chronic nicotine treatment counteracts dopamine D2 receptor upregulation induced by a partial meso-diencephalic hemitransection in the rat; Brain Res.; 655(1-2); pp. 25-32; Aug. 29, 1994.

Jarvik et al.; Inhibition of cigarette smoking by orally administered nicotine; Clinical Pharmacology and Therapeutics; 11(4); pp. 574-576; Jul. 1, 1970.

Jeyarasasingam et al.; Nitric oxide is involved in acetylcholinesterase inhibitor-induced myopathy in rats; The Journal of Pharmacology and Experimental Therapeutics; 295(1); pp. 314-320; Oct. 1, 2000.

Jeyarasasingam et al.; Stimulation of non-o7 nicotinic receptors partially protects dopaminergic neurons from I-methyl-4-phenylpyridinium-induced toxicity in culture; Neuroscience; 109(2); pp. 275-285; Jan. 28, 2002.

Jeyarasasingam et al.; Tacrine, a reversible acetylcholinesterase inhibitor, induces myopathy; Neuroreport; 11(6); pp. 1173-1176; Apr. 27, 2000.

Kalish et al.; Prevention of contact hypersensitivity to topically applied drugs by ethacrynic acid: potential application to transdermal drug delivery; J. Controll Rel; 48(1); pp. 79-87; Sep. 1997.

Kalish et al.; Sensitization of mice to topically applied drugs: albuterol, chlorpheniramine, clonidine and nadolol; Contact Dermatitis; 35(2); pp. 76-82; Aug. 1996.

Kelton et al.; The effects of nicotine on Parkinson's disease; Brain Cognition; 43(1-3); pp. 274-282; Jun. 2000.

Kiwi Drug; Buy nicorette microtabs; 3 pages; retrieved from the internet (www.kiwidrug.com/search/nicorette_microtabs); on Jul. 26, 2018.

Kotwal; Enhancement of intophoretic transport of diphenhydramine hydrochloride thermosensitive gel by optimization of pH, polymer concentration, electrode design, and pulse rate; AAPS PharmSciTech; 8(4); pp. 320-325; Oct. 2007.

Kulak et al.; 5-lodo-A-85380 binds to oconotoxin Mil-sensitive nicotinic acetylcholine receptors (nAChRs) as well as 04j32* subtypes; Journal of Neurochemistry; 81(2); pp. 403-406; Apr. 1, 2002.

Kulak et al.; Declines in different pi* nicotinic receptor populations in monkey striatum after nigrostriatal damage; The Journal of Pharmacology and Experimental Therapeutics: 303(2); pp. 633-639; Nov. 1, 2002.

Kulak et al.; Loss of nicotinic receptors in monkey striatum after I-methyl-4-phenyl-1,2,3,6-tetrahydropyridine treatment is due to a decline in oconotoxin Mil sites; Molecular Pharmacology: 61(1); pp. 230-238; Jan. 1, 2002.

Kumar et al.; Levodopa-dyskinesia incidence by age of Parkinson's disease onset; Movement disorders; 20(3); pp. 342-344; Mar. 2005.

Kydonieus et al. (Editors); Biochemical Modulation of Skin Reactions; CRC Press; Boca Ratan, FL; pp. 9-10; Dec. 1999.

Labrecque, G. et al.; Chronopharmacokinetics; Pharmaceutical News; 4(2); pp. 17-21; (year of pub. sufficiently earlier than effective US filing date and any foreign priority date) 1997.

Lai et al.; Long-term nicotine treatment decreases striatal a6* nicotinic acetylcholine receptor sites and function in mice; Molecular Pharmacology; 67(5); pp. 1639-1647; May 1, 2005.

Lai et al.; Selective recovery of striatal 1251-a-conotoxinMII nicotinic receptors after nigrostriatal damage in monkeys; Neuroscience; 127(2); pp. 399-408; Dec. 31, 2004.

Lamberg; Chronotherapeutics: Implications for drug therapy; American Pharmacy; NS31(11); pp. 20-23; Nov. 1991.

Langston et al.; Investigating levodopa-induced dyskinesias in the parkinsonian primate; Annals of Neurology; 47(4 Suppl 1); pp. S79-S88; Apr. 2000.

Laser et al.; A review of micropumps; J. of Micromech. and Microeng.; 14; pp. R35-R64; Apr. 2004.

Lee et al.; A comprehensive review of opioid-induced hyperalgesia; Pain Physician; 14; pp. 145-161; Mar. 2011.

Lemay et al.; Lack of efficacy of a nicotine transdermal treatment on motor and cognitive deficits in Parkinson's disease; Prog Neuropsychopharmacol Biol Psychiatry; 28(1); pp. 31-39; Jan. 2004.

Lemmer; Clinical Chronopharmacology: The Importance of Time in Drug Treatment, in Ciba Foundation Symposium 183—Circadian Clocks and their Adjustment (eds. Chadwick and Ackrill); John Wiley & Sons, Inc.; pp. 235-253; Apr. 1995.

Lemmer; Implications of chronopharmacokinetics for drug delivery: antiasthmatics, H2-blockers and cardiovascular active drugs; Adv Drug Del Rev; 6(1); pp. 83-100; Jan./Feb. 1991.

Lemmer; The clinical relevance of chronopharmacology in therapeutics; Pharmacological Research; 33(2); pp. 107-115; Feb. 1996.

LeWitt et al.; New developments in levodopa therapy; Neurology; 62(No. 1, Suppl. 1); pp. S9-S16; Jan. 2004.

Lieber Man; Compressed tablets by direct compression; Pharmaceutical Dosage forms; vol. 1, 2nd ed.; Marcel Dekker Inc.; pp. 195-246; (the year of publication is sufficiently earlier than the effective U.S. filing date and any foreign priority date so that the particular month of publication is not in issue) 1989.

Lieberman; Compression—coated and layer tablets; Pharmaceutical Dosage forms; vol. 1, 2nd ed.; Marcel Dekker Inc.; pp. 266-271; (the year of publication is sufficiently earlier than the effective U.S. filing date and any foreign priority date so that the particular month of publication is not in issue) 1989.

Lundblad et al.; Cellular and behavioural effects of the adenosine A2a receptor antagonist KW-6002 in a rat model of I-DOPA-induces Dyskinesia; Journal of Neurochemistry; 84(6); pp. 1396-1410; Mar. 2003.

Madandla et al,; Voluntary running provides neuroprotection in rats after 6-hydroxydopamine injection into the medial forebrain bundle; Metabolic Brain Disease; 19(1-2); pp. 43-50; Jun. 2004.

Maillefer et al.; A high-performance silicon micropump for an implantable drug delivery system; 12th IEEE Int'l Conf. on Micro Electro Mechanical Systems; MEMS '99; Orlando, FL; pp. 541-546; Jan. 1999.

Matta et al.; Guidelines on nicotine dose selection for in vivo research; Psychopharmacology (Berl.); 190(3); pp. 269-319; Feb. 1, 2007.

McCallum et al,; Decrease in alpha3*/alpha6* nicotinic receptors in monkey brain after nigrostriatal damage; Molecular Pharmacology; 68(3); pp. 737-746; Sep. 2005.

McCallum et al.; Compensation in pre-synaptic dopaminergic function following nigrostriatal damage in primates; Journal of Neurochemistry: 96(4); pp. 960-972; Feb. 1, 2006.

McCallum et al.; Differential regulation of mesolimbic alpha 3/alpha 6 beta 2 and aplha 4 beta 2 nicotinic acetylcholine receptor sites and function after long-term oral nicotine to monkeys; The Journal of Pharmacology and Experimental Therapeutics; 318(1); pp. 381-388; Jul. 2006.

McCallum et al.; Increases in aplha 4* but not aplha3*/alpha6* nicotinic receptor sites and function in the primate striatum following chronic oral nicotine treatment; Journal of Neurochemistry; 96(4); pp. 1028-1041; Feb. 2006.

McNeil Sweden AB. Package Leaflet: Information for the user. Nicorette Microtab Lemon 2mg sublingual tablets. (This leaflet was last approved in Apr. 16, 2008). retrived from ( www.lakemedelsverket. se/SPC_PIL/Pdf/enhumpil/Nicorette%20Microtab%20Lemon%202mg%20sublingual%20tablet%20ENG.pdf.) Accessed Aug. 19, 2010.

Medtronic; MiniMed Paradigm® Veo(TM) System (product info.); retrieved May 12, 2015from the internet: (http://www.medtronic.co.uk/your-health/diabetes/device/insulin-pumps/paradigm-veo-pump/); 3 pgs.

(56) References Cited

OTHER PUBLICATIONS

Meissner et al.; Priorities in parkinson's disease research; Nature reviews Drug Discovery; 10(5); pp. 377-393; May 1, 2011.

Menzaghi et al.; Interactions between a novel cholinergic ion channel against, SIB-1765F anf L-DOPA in the reserpine model of parkinson's disease in rats; Journal of Pharmacology and Experimental Therapeutics: 280 (1); pp. 393-401; Jan. 1, 1997.

MERCK manual of therapy and diagnosis; 17th edition. Merck Research Laboratories; pp. 1466-1471; (the year of publication is sufficiently earlier than the effective U.S. filing date and any foreign priority date so that the particular month of publication is not in issue) 1999.

Meredith et al.; Behavioral models of Parkinson's disease in rodents: a new look at an old problem; Movement Disorders; 21(10); pp. 1595-1606; Oct. 1, 2006.

Meshul et al.; Nicotine Affects Striatal Glutamatergic Function in 6-OHDA Lesioned Rats; Advanced in behavioural Biology. Basal Ganglia VI.; Springer, Boston, MA.; vol. 54; pp. 589-598; the year of publication is sufficiently earlier than the effective U.S. filing date and any foreign priority date so that the particular month of publication is not in issue) 2002.

Meshul et al.; Nicotine alters striatal glutamate function and decreases the apomorphine-induced contralateral rotations in 6-OHDA-lesioned rats; Experimental Neurology; 175(1); pp. 257-274; May 31, 2002.

Molander et al.; Reduction of tobacco withdrawal symptoms with a sublingual nicotine tablet: A placebo controlled study; Nictonie & Tob. Res.; 2(2); pp. 187-191; May 2000.

Murphy et al.; Transdermal drug delivery systems and skin sensitivity reactions. Incidence and management; Am. J. Clin Dermatol.; 1(6); pp. 361-368; Nov./Dec. 2000.

Mutalik et al.; Glibenclamide transdermal patches: physicochemical, pharmacodynamic, and pharmacokinetic evaluation; J Pharm Sci; 93(6); pp. 1577-1594; Jun. 2004.

Mutalik et al.; Glipizide matrix transdermal systems for diabetes mellitus: preparation, in vitro and preclinical studies; Life Sci; 79(16; pp. 1568-1567; Sep. 2006.

Nakadate et al.; Effects of chalcone derivatives on lipoxygenase and cyclooxygenase activities of mouse epidermis; Prostaglandins; 30(3); pp. 357-368; Sep. 1985.

National Institute of Neurological Disorders and Stroke. Parkinson's Disease: Hope Through Research. 54 pages; Retrieved from the internet (https://catalog.ninds.nih.gov/pubstatic//15-139/15-139. pdf) on Jan. 15, 2018.

Newhouse et al.; Nicotine treatment of mild cognitive impairment: a 6-month double-blind pilot clinical trial; Neurology; 78(2); pp. 91-101; Jan. 10, 2012.

Newmark; Plant phenolics as potential cancer prevention agents; Chapter 3 in Dietary Phytochemicals in Cancer Prevention; Chap. 3; Adv. Exp. Med. Biol. 401; pp. 25-34; © 1996.

Ohdo; Changes in toxicity and effectiveness with timing of drug administration: implications for drug safety; Drug Safety; 26(14); pp. 999-1010; Dec. 2003.

Olanow; The scientific basis for the current treatment of Parkinson's disease; Annu. Rev. Med.; 55; pp. 41-60; Feb. 18, 2004.

Olsson et al.; A valve-less planar pump in silicon; IEEE; The 8th International Conference on Solid-State Sensors and Actuators; vol. 2; pp. 291-294, Jun. 1995.

Olsson et al.; An improved valve-less pump fabricated using deep reactive Ion etching; Proc. of the IEEE, 9th Int'l Workshop on MEMS; San Diego, CA; pp. 479-484; Feb. 11-15, 1996.

O'Neill et al.; The role of neuronal nicotinic acetylcholine receptors in acute and chronic neurodegeneration; Current Drug Targets—CNS and Neurological Disorders; 1(4); pp. 399-412; Aug. 1, 2002.

Parkinson Study Group; Levodopa and the progression of Parkinson's disease; N Engl J Med.; 351; pp. 2498-2508; Dec. 9, 2004.

Petzinger et al.; Reliability and validity of a new global dyskinesia rating scale in the MPTP-lesioned non-human primate; Movement Disorders; 16(2); pp. 202-207; Mar. 1, 2001.

Priano et al.; Nocturnal anomalous movement reduction and sleep microstructure analysis in parkinsonian patients during 1-night transdermal apomorphine treatment; Neurol Sci.; 24(3); pp. 207-208; Oct. 2003.

Prosise et al.; Effect of abstinence from smoking on sleep and daytime sleepiness; Chest; 105(4); pp. 1136-1141; Apr. 1994.

Quik et al.; Chronic oral nicotine normalizes dopaminergic function and synaptic plasticity in I-methyl-4-phenyl-1,2,3,6-tetrahydropyridine-lesioned primates; The Journal of Neuroscience; 26(17); pp. 4681-4689; Apr. 26, 2006.

Quik et al.; Chronic oral nicotine treatment protects against striatal degeneration in MPTP-treated primates; Journal of Neurochemistry; 98(6); pp. 1866-1875; Sep. 1, 2006.

Quik et al.; Differential alterations in nicotinic receptor a6 and /33 subunit messenger RNAs in monkey substantia nigra after nigrostriatal degeneration; Neuroscience; 100(1); pp. 63-72; Sep. 7, 2000.

Quik et al.; Differential declines in striatal nicotinic receptor subtype function after nigrostriatal damage in mice; Molecular Pharmacology; 63(5); pp. 1169-1179; May 1, 2003.

Quik et al.; Differential nicotinic receptor expression in monkey basal ganglia: Effects of nigrostriatal damage; Neuroscience; 112(3); pp. 619-630; Jul. 5, 2002.

Quik et al.; Expression of D3 receptor messenger RNA and binding sites in monkey striatum and substantia nigra after nigrostriatal degeneration: Effect of levodopa treatment.;Neuroscience; 98(2); pp. 263-273; Jun. 30, 2000.

Quik et al.; Increases in striatal preproenkephalin gene expression are associated with nigrostriatal damage but not L-DOPA-induced dyskinesias in the squirrel monkey; Neuroscience; 113(1); pp. 213-220; Aug. 2, 2002.

Quik et al.; L-DOPA treatment modulates nicotinic receptors in monkey striatum; Mol Pharmacol; 64(3); pp. 619-628; Sep. 2003.

Quik et al.; Localization of nicotinic receptor subunit mRNAs in monkey brain by in situ hybridization; The Journal of Comparative Neurology; 425(1); pp. 58-69; Sep. 11, 2000.

Quik et al.; Loss of a-conotoxinMII- and A85380-sensitive nicotinic receptors in Parkinson's disease striatum; Journal of Neurochemistry; 88(3); pp. 668-679; Feb. 1, 2004.

Quik et al.; Nicotine administration reduces striatal MPP+ levels in mice; Brain Research; 917(2); pp. 219-224; Nov. 2, 2001.

Quik et al.; Nicotine and nicotinic receptors; relevance to Parkinson's disease; Neurotoxicology; 23(4-5); pp. 581-594; Oct. 2002.

Quik et al.; Nicotine and Parkinson's disease: implications for therapy; Movement Disorders; 23(12); pp. 1641-1652; (Author Manuscript); Sep. 1, 2008.

Quik et al.; Nicotine as a potential neuroprotective agent for Parkinson's disease; Movement disorders; 27(8); pp. 947-957; Jul. 1, 2012.

Quik et al.; Nicotine neuroprotection against nigrostriatal damage: importance of the animal model; Trends in Pharmacological sciences; 28(5); pp. 229-235; May 31, 2007.

Quik et al.; Nicotine reduces levodopa-induced dyskinesias in lesioned monkeys; Annals of neurology; 62(6); pp. 588-596; (Author Manuscript); Dec. 1, 2007.

Quik et al.; Nicotinic receptors and Parkinson's disease; European Journal of Pharmacology; 393(1); pp. 223-230; Mar. 30, 2000.

Quik et al.; Striatal a6* nicotinic acetylcholine receptors: Potential targets for Parkinson's disease therapy; The Journal of Pharmacology and Experimental Therapeutics; 316(2); pp. 481-489; Feb. 1, 2006.

Quik et al.; Subunit composition of nicotinic receptors in monkey striatum: Effect of treatments with I-methyl-4-phenyl-I,2,3,6-tetrahydropyridine or L-DOPA; Molecular Pharmacology; 67(1); pp. 32-41; Jan. 2005.

Quik et al.; Vulnerability of 125I-a-conotoxin Mil binding sites to nigrostriatal damage in monkey; The Journal of Neuroscience; 21(15); pp. 5494-5500; Aug. 1, 2001.

Quik; Smoking, nicotine and Parkinson's disease; Trends in Neurosciences; 27(9); pp. 561-568; Sep. 2004.

Redfern et al.; Circadian rhythms, jet lag, and chronobiotics: An overview; Chronobiology International; 11(4); pp. 253-265; Aug. 1994.

(56) References Cited

OTHER PUBLICATIONS

Reinberg; Concepts of Circadian Chronopharmacology; Annals of the New York Academy of Sciences; 618 (Temporal Control of Drug Delivery); pp. 102-115; Feb. 1991.

Rueter et al.; ABT-089: Pharmacological properties of a neuronal nicotinic acetylcholine receptor agonist for the potential treatment of cognitive disorders; CNS Drug Reviews; 10(2); pp. 167-182; Jun. 1, 2004.

Samii et al.; Parkinson's disease; The Lancet; 363(9423); pp. 1783-1793; May 29, 2004.

Savitt et al.; Diagnosis and treatment of Parkinson disease: molecules to medicine; The Journal of Clinical Investigation; 116(7); pp. 1744-1754; Jul. 3, 2006.

Schapira; Disease modification in Parkinson's disease; The Lancet Neurology; 3(6); pp. 362-368; Jun. 30, 2004.

Schneider et al.; Effects of SIB-1508Y, a novel neuronal nictonic acetylcholine receptor agonist, on motor behavior in parkinsonian monkeys; Movement Disorders; 13(4); pp. 637-642; Jul. 1, 1998.

Schneider et al.; Effects of the nicotinic acetylcholine receptor agonist SIB-1508Y on object retrieval performance in MPTP-treated monkeys: Comparison with levodopa treatment; Annals of Neurology: 43(3); pp. 311-317; Mar. 1, 1998.

Schober et al.; Classic toxin-induced animal models of Parkinson's disease: 6-OHDA and MPTP; Cell and Tissue Research; 318(1); pp. 215-224; Oct. 1, 2004.

Shin et al.; Enhanced bioavailability of triprolidine from the trans-dermal TPX matrix system in rabbits; Int. J. Pharm.; 234(1-2); pp. 67-73; Mar. 2002.

Silver et al.; Transdermal nicotine and haloperidol in Tourette's disorder: a double-blind placebo-controlled study; Journal of Clinical Psychiatry; 62(9); pp. 707-714; Sep. 1, 2001.

Singer et al.; Nightmares in patients with Alzheimer's disease caused by donepezil: Therapeutic effect depends on the time of intake; Nervenarzt; 76(9); pp. 1127-1129; Sep. 2005 (Article in German w/ Eng. Summary).

Star Micronics Co., Ltd; Prototype Diaphragm Micro Pump SDMP305 (specifications); retrieved May 12, 2015 from the internet archive as of Jul. 2006 (http://www.star-m.jp/eng/products/develop/de07.htm); 3 pgs.

Stocchi et al.; Motor fluctuations in levodopa treatment: clinical pharmacology; European Neurology; 36(Suppl 1); pp. 38-42; Jan. 1996.

Strong et al.; Genotype and smoking history affect risk of levodopa-induced dyskinesias in parkinson's disease; Movement Disorders; 21(5); pp. 654-659; May 1, 2006.

Thiele et al. (Ed.); Oxidants and Antioxidants in Cutaneous Biology: Current Problems in Dermatology (Book 29); S. Karger; 196 pgs.; Feb. 2001.

Togasaki et al.; Dyskinesias in normal squirrel monkeys induced by nomifensine and levodopa; Neuropharmacology; 48(3); pp. 398-405; Mar. 31, 2005.

Togasaki et al.; Levodopa induces dyskinesias in normal squirrel monkeys; Annals of Neurology; 50(2); pp. 254-257; Aug. 1, 2001.

Togasaki et al.; The Webcam system: A simple, automated, computer-based video system for quantitative measurement of movement of nonhuman primates; Journal of Neuroscience Methods; 145(1); pp. 159-166; Jun. 30, 2005.

Tolosa et al.; Antagonism by piperidine of levodopa effects in Parkinson disease; Neurology; 27(9); pp. 875-877; Sep. 1, 1977.

U.S. Department of Health and Human Services, Food and Drug Administration, Center for Drug Evaluation and Research (CDER); Guidance for industry: Abuse-deterrent opioids—Evaluation and labeling; 24 pages; retrieved from the internet (http://www.fda.gov/downloads/drugs/guidancecomplainceregulatoryinformation/guidances/ucm344743.pdf); Jan. 2013.

United States of America VA/DoD; Tapering and discontinuing opioids; 2 pages; retrieved from the internet (http://www.healthquality.va.gov/guidelines/Pain/cot/OpioidTaperingFactSheet23May2013v1.pdf); on Sep. 1, 2016.

Vieregge et al.; Transdermal nicotine in PD: A randomized, double-blind, placebo-controlled study; Neurology; 57(6); pp. 1032-1035; Sep. 25, 2001.

Villafane et al.; Long-term nicotine administration can improve Parkinson's disease: report of a case after three years of treatment; Revista Neurologica Argentina; 27(2); pp. 95-97; (the year of publication is sufficiently earlier than the effective U.S. filing date and any foreign priority date so that the particular month of publication is not in issue) 2002.

Warburton et al.; Facilitation of learning and state dependency with nicotine; Psychopharmacology; 89(1); pp. 55-59; May 1, 1986.

Wermuth et al.; Glossary of terms used in medicinal chemistry Pure & Appl. Chem., vol. 70(5); 1129-1143; 1998 AC recommendations 1998); Pure and Applied Chemistry; 70(5); pp. 1129-1143; Jan. 1998.

Wesnes et al.; Effects of scopolamine and nicotine on human rapid information processing performance; Psychopharmacology; 82(3); pp. 147-150; Sep. 1, 1984.

Westman et al.; Oral nicotine solution for smoking cessation: a pilot tolerability study; Nicotine and Tobacco Research; 3(4); pp. 391-396; Nov. 1, 2001.

Wille et al.; cis-urocanic Acid Induces Mast Cell Degranulation and Release of Preformed TNF-alpha: A Possible Mechanism Linking UVB and cis-urocanic Acid to Immunosuppression of Contact Hypersensitivity; Skin Pharm Appl Skin Physiol; 12(1-2); pp. 18-27; Jan. 1999.

Wille et al.; Inhibition of irritation and contact hypersensitivity by ethacrynic acid, Skin Pharm Appl Skin Physiol; 11(4-5); pp. 279-288; Jul. 1998.

Wille et al.; Inhibition of Irritation and Contact Hypersensitivity by Phenoxyacetic Acid Methyl Ester in Mice; Skin Pharm Appl Skin Physiol; 13(2); pp. 65-74; Mar. 2000.

Wille et al.; Several different ion channel modulators abrogate contact hypersensitivity in mice; Skin Pharm Appl Skin Physiol; 12(1-2); pp. 12-17; Jan. 1999.

Wille, J.; Novel topical delivery system for plant derived hydro-phobic anti-irritant active (presentation abstract No. 273); 226th ACS National Meeting; New York, NY; Sep. 7-11, 2003.

Wille; In Closing: an editorial on Plant-Derived Anti-irritants. Cosmetics & Toiletries, 118 (8), Aug. 2003.

Wille; Novel plant-derived anti-irritants; (presented Dec. 5-6, 2002 at the 2002 Ann. Scientific Mtg. & Tech. Showcase); J. Cosmet. Sci.; 54; pp. 106-107; Jan./Feb. 2003.

Wille; Thixogel: Novel topical delivery system for hydrophobic plant actives; in ROSEN (Ed.) Delivery System Handbook for Personal Care and Cosmetic Products; 1st Ed.; ISBN: 978-0-8155-1504-3; pp. 762-794; Sep. 2005.

Youan; Chronopharmaceutics: gimmick or clinically relevant approach to drug delivery?; J Cont Rel; 98(3); pp. 337-353; Aug. 2004.

Yun et al.; A distributed memory MIMD multi-computer with reconfigurable custom computing capabilities; IEEE; Proc. Int'l. Conf. on Parallel and Distributed Systems; pp. 8-13; Dec. 10-13, 1997.

Zubieta et al.; Placebo effects mediated by endogenous opioid activity on mu-opioid receptors; 25(34); pp. 7754-7762; Aug. 24, 2005.

Netzel et al.; U.S. Appl. No. 17/815,879 entitled "Drug Delivery methods and systems," filed Jul. 28, 2022.

* cited by examiner

OPTIMIZED BIO-SYNCHRONOUS BIOACTIVE AGENT DELIVERY SYSTEM

CROSS REFERENCE TO RELATED APPLICATIONS

The present application is a continuation application of U.S. patent application Ser. No. 16/165,720, filed Oct. 19, 2018, now U.S. Patent Publication No. 2019/0054235, which is a divisional application of U.S. patent application Ser. No. 14/156,998, filed Jan. 16, 2014, now U.S. Pat. No. 10,105,487; which application relates to and claims the benefit of priority to U.S. Provisional Patent Application No. 61/756,339 filed Jan. 24, 2013, entitled "Optimized Biosynchronous Transdermal Drug Delivery", all of which are hereby incorporated by reference in their entirety for all purposes as if fully set forth herein.

STATEMENT OF GOVERNMENT SUPPORT

This invention was made with Government support under Grant No. R44CA171786 awarded by the National Institutes of Health. The Government has certain rights in the invention.

BACKGROUND OF THE INVENTION

Field of the Invention

Embodiments of the present invention relate, in general, to bio-synchronous bioactive agent delivery of a bioactive agent and more particularly to methodology and systems for individualization and optimization of bio-synchronous bioactive agent delivery of a bioactive agent.

Relevant Background

In the field of drug delivery, it is recognized that supplying the drug in a correct temporal pattern is an important attribute of any drug delivery methodology. Controlled release drug delivery systems are intended to improve response to a drug and/or lessen side effects of a drug. The term "controlled release" refers generally to delivery mechanisms that make an active ingredient available to the biological system of a host in a manner that supplies the drug according to a desired temporal pattern. Controlled release drug delivery may be implemented using instantaneous release systems, delayed release systems, and sustained release systems. In most cases, controlled release systems are designed to maintain a sustained plasma level of an active ingredient in a drug within a human or animal host over a period of time.

Instantaneous release refers to systems that make the active ingredient available immediately after administration to the bio-system of the host. Instantaneous release systems include continuous or pulsed intravenous infusion or injections. Such systems provide a great deal of control because administration can be both instantaneously started and stopped and the delivery rate can be controlled with great precision. However, the administration is undesirably invasive as they involve administration via a puncture needle or catheter. 'Delayed release' refers to systems in which the active ingredient made available to the host at some time after administration. Such systems include oral as well as injectable drugs in which the active ingredient is coated or encapsulated with a substance that dissolves at a known rate so as to release the active ingredient after the delay. Unfortunately, it is often difficult to control the degradation of the coating or encapsulate after administration and the actual performance will vary from patient to patient. Sustained release generally refers to release of active ingredient such that the level of active ingredient available to the host is maintained at some level over a period of time. Like delayed release systems, sustained release systems are difficult to control and exhibit variability from patient to patient. Due to the adsorption through the gastrointestinal tract, drug concentrations rise quickly in the body when taking a pill, but the decrease is dependent on excretion and metabolism, which cannot be effectively controlled. In addition, the adsorption through the gastrointestinal tract in many cases leads to considerable side effects (such as ulcers), and can severely damage the liver.

Transdermal drug delivery has developed primarily for sustained release of drugs in situations where oral sustained release systems are inadequate. In some cases, drugs cannot be effectively administered orally because the active ingredients are destroyed or altered by the gastrointestinal system. In other cases the drug may be physically or chemically incompatible with the coatings and/or chelating agents used to implement sustained release. In other cases a transdermal delivery system may provide sustained release over a period of days or weeks whereas orally administered drugs may offer sustained performance over only a few hours. A wide variety of active substances can be delivered through transdermal systems so long as the active substance can be provided in a form that can cross the skin barrier.

In most cases transdermal delivery systems are passive, taking the form of a patch that is adhesively attached to the host. The patch includes a quantity of the active substance, along with a suitable carrier if need be, absorbed in a sponge or similar system. Once applied, the active ingredient diffuses into the host through the skin at a rate determined by the concentration of the active substance and the diffusivity of the active substance. However, a variety of physical and chemical processes at the skin/patch boundary affect the delivery rate and may eventually inhibit drug delivery altogether. Active transdermal delivery systems have been developed to help regulate the delivery rate by providing mechanisms to improve drug delivery over time by "pumping" the active ingredient. One such system is described in U.S. Pat. No. 5,370,635 entitled "DEVICE FOR DELIVERING A MEDICAMENT" which describes a system for delivering a medicament and dispensing it to an organism for a relatively long period of time, for example at least a few days. The device can be adapted for positioning on the surface of the skin of a human or possibly an animal body in order to apply a medicament thereto from the outer side thereof.

Conventional transdermal systems circumvent the disadvantages of the adsorption through the gastrointestinal tract, but they do not optimize or tailor the dosing regiment to offset peak symptoms. In addition the constant transdermal delivery of a drug can lead to severe side effects, including debilitating sleep disorders and ever increasing tolerance.

Timed delivery is most often used to maintain a sustained level of a drug in the body. A significant focus of current research in drug delivery has been to determine the influence of a patient's circadian or other biological rhythms on drug efficacy and efficiency. This research demonstrates that certain disease symptoms follow a daily pattern, with peak symptoms at certain times of the day. It has been widely acknowledged that hormones, neurotransmitters and other intra-body compounds are released in different amounts at different times of the day pursuant to daily patterns. The Wall Street Journal reported on May 27, 2003 that "Doctors are increasingly looking at the clock when it comes to prescribing medicine, instructing patients not only to what drug to use but also precisely when to take it. This new approach stems from a growing body of research that demonstrates that certain diseases tend to get worse at certain times of the day. By synchronizing medications with a patient's body clock, many physicians believe that the drugs will work more effectively and with fewer side effects. In some cases, the improvements have been so pronounced that doctors have been able to reduce dosages." Similarly, American Pharmacy reports, "Circadian physiologic processes alter drug absorption, distribution, metabolism, and excretion. As a result, drug doses need to be adjusted to meet the differing needs of target organs or tissues at various times of the day."

Recently, an orally administered drug for arthritis treatment has suggested a chrono-therapeutic approach using a delay release system where the delay is scheduled to release the active ingredient at the beginning of an interleukin 6 cascade that is believed to cause early morning stiffness in rheumatoid arthritis patients. By attempting to synchronize the drug delivery with a biological cycle it is believed that low doses may be used to achieve desired results. However, this system does not overcome the limitations of delayed release systems described above. Although it may be possible to meet the requirements of chrono-pharmacology with pills, such an effort requires an enormous amount of discipline by the patient to comply with the treatment regiment. For example, to achieve optimal results, many patients may need to wake up during the night to take their medication.

Currently, patient compliance (taking the proper dosages at the prescribed times) is a critical problem facing caregivers and pharmaceutical firms alike. Studies show that only about half of patients take medications at the times and in the dosages directed by their physician. It is reported that each year, 125,000 deaths and up to 20% of all hospital and nursing home admissions result from patient non-compliance. And it is estimated that non-compliance results in additional healthcare costs in excess of $100 billion per year in United States. These figures are even more pronounced for the elderly. Hence, a need exists for systems and methods that increase patient compliance as well as administration of a variety of drugs.

One successful Chrono-Therapeutic approach involves synchronizing the administration of compounds with the human body's natural circadian rhythms and addiction rhythms to counteract symptoms when they are likely to be at their worst by using an automated transdermal or other drug administration system. As described in U.S. Pat. No. 7,780,981, "Biosynchronous Transdermal Drug Delivery", a device delivers varying dosages at varying times, pursuant to a pre-programmed dosage profile. This ensures that peak drug concentrations are present in the bloodstream to offset peak disease and/or addiction symptoms arising from variances and fluctuation in the body's natural circadian rhythms.

While the '981 patent is a tremendous advance in transdermal drug application, the determination of an individuals circadian and biologic rhythm can be a challenge. Moreover, for the efficacy of the treatment protocol to be maximized, the delivery of the pharmacology must be aligned with the needs of each individual. As there is a finite and determinable amount of time from the point of delivery of the drug to its effect, the chosen drug would ideally be delivered immediately prior to the onset of a symptom such as an addictive craving. Accordingly identifying, predicting the onset of a symptom, a craving, and its intensity, is a necessary component to effective addiction cessation treatment. Furthermore, once identified these physiologically and psychological demands must be converted to an individualized dosage profile to optimize efficacy.

It is also widely recognized that the physiological characteristics of an illness also have a psychological effect on a patient and, likewise, that a patient's psychological condition can directly impact one's physiological health. Yet treatment protocols often fail to take into account these two closely interrelated aspects of healthcare. It is widely accepted that emotional support offered by help lines or group discussions can assist an individual to overcome the conditions associated with a physical ailment. Nine-step programs and the like have resounding success regarding addictive related conditions yet few such programs are integrated into pharmacological treatment protocols. What is needed therefore is a comprehensive treatment regime that combines a temporally appropriate and biometrically synchronized pharmacological treatment, the ability to monitor a patient's compliance with the treatment plan, and suitable emotional support. These and other challenges of the prior art are addressed by one or more embodiments of the present invention.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

SUMMARY OF THE INVENTION

A system and associated methodology for an optimized bio-synchronous drug delivery begins with establishing a bio-synchronous treatment protocol that incorporates individual temporal and innate biological characteristics into a pharmacological treatment plan. The bio-synchronous treatment protocol is thereafter initiated by the user, or associated healthcare provider using, in one embodiment a bioactive agent delivery device. The bio-synchronous drug delivery system and methodology further includes continually gathering patient data during the bio-synchronous treatment protocol including physical, psychological, temporal and environmental characteristics. Once collected this data is analyzed so to not only determine an initial treatment protocol but to also determining whether modification to the ongoing bio-synchronous treatment protocol is required. And, responsive to determining modification to the bio-synchronous treatment protocol is required the system modifies the bio-synchronous treatment protocol and use of the bio-synchronous bioactive agent delivery device and then iteratively assesses its optimization to see if additional modifications are warranted.

Other features of the present invention include temporal administration of pharmacological elements based on individual patient temporal patterns and/or on patient innately rhythmic biological processes. The bio-synchronous treatment protocol of the present invention also includes temporal psychological support that can be linked to patient's temporal patterns or linked to patient's innately rhythmic biological processes. Moreover, temporal psychological support can be proactively based on the bio-synchronous treatment protocol or reactive based on a patient's current emotional state. This temporal psychological support can include an electronic message, direct interaction with psychological support personnel and the like.

The optimized bio-synchronous bioactive agent deliver device of the present invention further includes the ability to monitor compliance with the bio-synchronous treatment protocol and collect patient physiological data and patient psychological data. Such data can include, for example, a patient reported emotion such a craving, intense anxiety, or pain.

Using this information the present invention can modify the current treatment protocol, including, in one embodiment, modifying the administration of the protocol remotely.

Another embodiment of the present invention includes method for optimized bio-synchronous drug delivery of a bio-synchronous treatment protocol that includes the steps of collecting patient data during use of a bio-synchronous bioactive agent delivery device according to the bio-synchronous treatment protocol, analyzing the collected data during ongoing use of the bio-synchronous bioactive agent delivery device, and, if necessary, modifying the bio-synchronous treatment protocol. All of which is done during use of the bio-synchronous bioactive agent delivery device.

In addition to the methodology described above the present invention, in one embodiment, further includes a system for optimized bio-synchronous drug delivery. Such a system can include, a bio-synchronous treatment protocol and an associated bio-synchronous bioactive agent delivery device configured to administer pharmacological elements of the bio-synchronous treatment protocol. The system also includes patient data gathered during administration of the bio-synchronous treatment protocol that is analyzed by an analysis module and which is further operable to optimize the bio-synchronous treatment protocol based on that analysis.

Such a system can also include a communication module operable to communicate (wirelessly in some embodiments) the modified bio-synchronous treatment protocol to the delivery device. Such a bio-synchronous treatment protocol can include pharmacological elements temporally administered based on individual patient temporal patterns and/or individual patient innately rhythmic biological processes.

The system also can include, in other embodiments, temporal psychological support engine or module. This support module and its associated processes can be linked to patient temporal patterns and/or to patient innately rhythmic biological processes. The psychological support module can further be proactively initiated on the bio-synchronous treatment protocol as well as reactive to address immediate patent needs. In one version of the present invention temporal psychological support includes electronic messages or direct interaction with psychological support personnel.

Another feature of the present invention the ability to gather patient compliance, physiological and psychological data and when warranted, modify the current and ongoing treatment protocol. The system can include applications resident on a smart phone or similar device that can record and report patient physiological/physiological data such as a craving, anxiety or experience of intense pain. Using this, and other, information, the system of the present invention can not only offer emotional support, but also modify the ongoing treatment protocol to provide an optimized bio-synchronous bioactive agent delivery system.

The features and advantages described in this disclosure and in the following detailed description are not all-inclusive. Many additional features and advantages will be apparent to one of ordinary skill in the relevant art in view of the drawings, specification, and claims hereof. Moreover, it should be noted that the language used in the specification has been principally selected for readability and instructional purposes and may not have been selected to delineate or circumscribe the inventive subject matter; reference to the claims is necessary to determine such inventive subject matter.

BRIEF DESCRIPTION OF THE DRAWINGS

The aforementioned and other features and objects of the present invention and the manner of attaining them will become more apparent, and the invention itself will be best understood, by reference to the following description of one or more embodiments taken in conjunction with the accompanying drawings, wherein:

FIG. 3, are high level flowcharts of a method for transdermal drug delivery optimization and emotional support according to one embodiment of the present invention;

Figure 1:
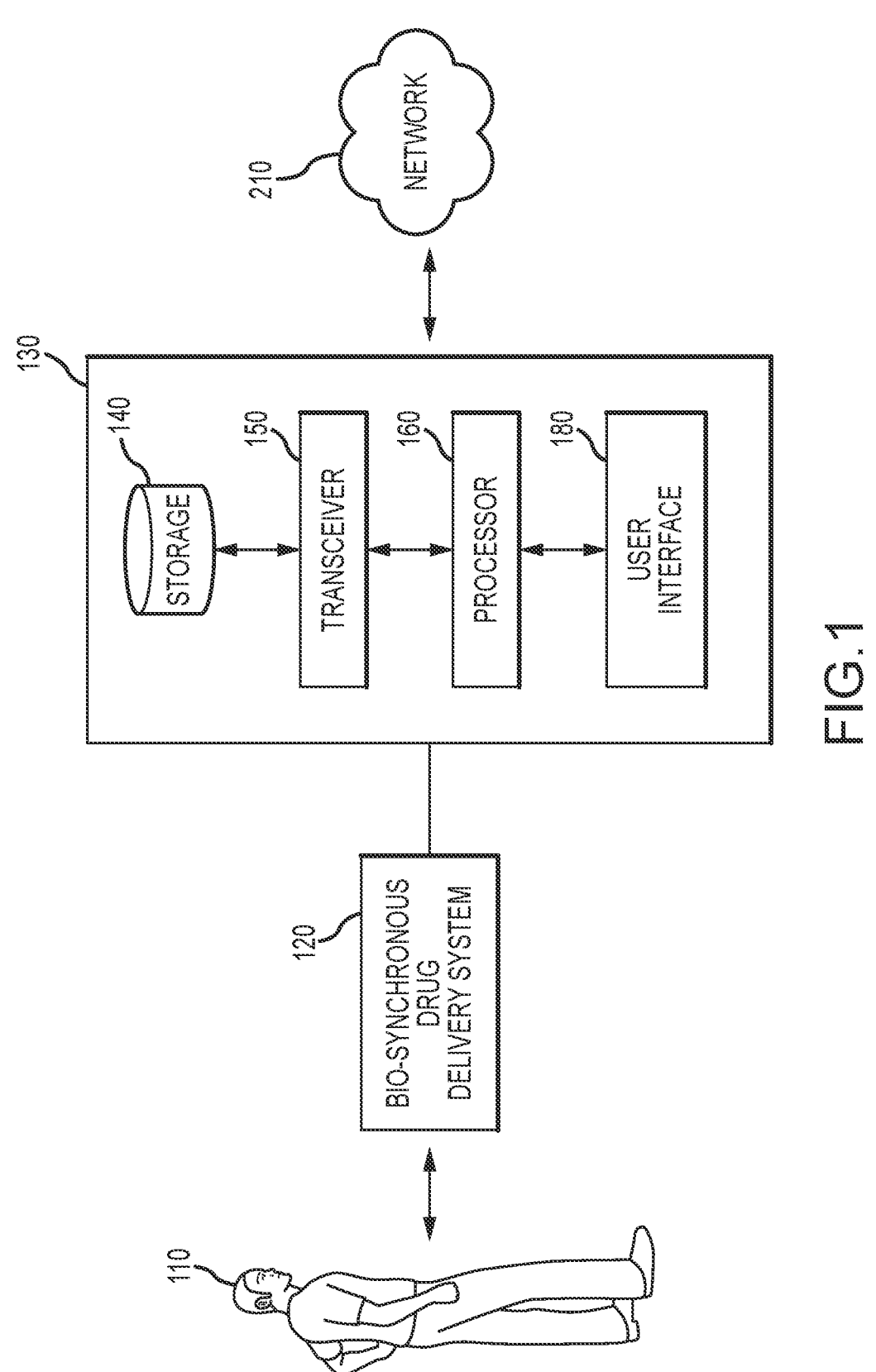
FIG. 1 is a high level system diagram of an environment for the use of an optimized bio-synchronous bioactive agent delivery system according to one embodiment of the present invention.

The Figures depict embodiments of the present invention for purposes of illustration only. Like numbers refer to like elements throughout. In the figures, the sizes of certain lines, layers, components, elements or features may be exaggerated for clarity. One skilled in the art will readily recognize from the following discussion that alternative embodiments of the structures and methods illustrated herein may be employed without departing from the principles of the invention described herein.

DESCRIPTION OF THE INVENTION

Research demonstrates that certain disease symptoms follow a daily pattern, with peak symptoms at certain times of the day. It has been widely acknowledged that hormones, neurotransmitters and other intra-body compounds are released in different amounts at different times of the day pursuant to daily patterns. These temporal symptoms are vividly apparent in addiction ailments. For example, according to studies performed, immediately upon waking, smokers typically have peak nicotine cravings. These peak cravings return after each meal, due to the interplay of serotonin release as a trained response to the culmination of a meal. Precisely timing the administration of addiction cessation drugs so that they reach peak levels when symptoms are likely to be at their worst, greatly improves the efficacy of these drugs.

Critical to the administration of these drugs is the accurate and individualistic temporal determination regular and peak craving episodes. The present invention provides a means by which symptoms, cravings and desires, are individualistically identified to form a dosage profile. In addition to identifying when a symptom occurs, such as a craving, and its intensity, the present invention gathers other vital information so as to modify (wirelessly in some embodiments) the administration drug administration profile to be maximally effective. According to one embodiment of the present invention a digital application presents a user interface that enables a user to quickly and effectively input time sensitive data related to a particular symptom. Using a device such as smartphone, PDA or the like, a user can, upon experiencing a symptom, memorialize and convey the experience. The application in one embodiment can assist the user in identifying the intensity of the symptom as well as logging when the symptom occurred. Using that data, along with additional profile data of the user, a drug delivery or treatment protocol can be determined and thereafter delivered to a drug delivery device for execution.

Cessation and treatment of addictive behavior is of but one application of the advances associated as in the present invention. While the description that follows often describes the invention with reference to the cessation of an addictive behavior, smoking for example, on of reasonable skill in the relevant art will recognize that the features of the present invention are equally applicable access a wide range of disease treatment protocols. For example, the same advances described herein can be used to improve and optimize treatment for cardiac disease, diabetes, psychotic episodes, pain management, and the like. The present description is provided by way of example and the focus on smoking cessation should not be interpreted as limiting the invention.

Embodiments of the present invention further enhance the efficacy of the drug treatment protocols by providing real time psychological and emotional support. Addiction and smoking cessation support groups for example remain available to the users of the present invention however these types of support mechanisms are enhanced with the utilization of social media and follow up patient interface of the present invention. Websites and social media services such as Facebook® and Twitter® can provide access to smoking cessation tools when properly accessed and chat rooms, hot-lines, tips and so on can provide the user with emotional support in addition to the pharmacological assistance to overcome the urge to smoke. The present invention, upon gaining information leading to the determination of a immediate symptom, a craving or aberrant desire to smoke in the case of addiction to nicotine, can not only modify the drug treatment protocols but provide the user with a supportive tip, text, voice mail, vibrating tone, or any other for of communicative message, to support their emotional need to repel the craving and follow the treatment protocol.

Embodiments of the present invention are hereafter described in detail with reference to the accompanying Figures. Although the invention has been described and illustrated with a certain degree of particularity, it is understood that the present disclosure has been made only by way of example and that those skilled in the art can resort to numerous changes in the combination and arrangement of parts without departing from the spirit and scope of the invention.

Reference to the accompanying drawings is provided to assist in a comprehensive understanding of exemplary embodiments of the present invention as defined by the claims and their equivalents. The specification includes various specific details to assist in that understanding but these are to be regarded as merely exemplary. Accordingly, those of ordinary skill in the art will recognize that various changes and modifications of the embodiments described herein can be made without departing from the scope and spirit of the invention. Also, descriptions of well-known functions and constructions are omitted for clarity and conciseness.

The terms and words used in the following description and claims are not limited to the bibliographical meanings, but are merely used by the inventor(s) to enable a clear and consistent understanding of the invention. Accordingly, it should be apparent to those skilled in the art that the following description of exemplary embodiments of the present invention are provided for illustration purpose only and not for the purpose of limiting the invention as defined by the appended claims and their equivalents.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

Like numbers refer to like elements throughout. In the figures, the sizes of certain lines, layers, components, elements or features may be exaggerated for clarity.

The terminology used herein is for the purpose of describing particular embodiments only and is not intended to be limiting of the invention. It is to be understood that the singular forms "a," "an," and "the" include plural referents unless the context clearly dictates otherwise. Thus, for example, reference to "a component surface" includes reference to one or more of such surfaces.

By the term "substantially" it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of a device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Included in the description are flowcharts depicting examples of the methodology that may be used to determine individualized an optimized dosage profiles for bioactive agent delivery. In the following description, it will be understood that each block of the flowchart illustrations, and combinations of blocks in the flowchart illustrations, can be implemented by computer program instructions. These computer program instructions may be loaded onto a computer or other programmable apparatus to produce a machine such that the instructions that executes on the computer or other programmable apparatus create means for implementing the functions specified in the flowchart block or blocks. These computer program instructions may also be stored in a computer-readable memory that can direct a computer or other programmable apparatus to function in a particular manner such that the instructions stored in the computer-readable memory produce an article of manufacture including instruction means that implement the function specified in the flowchart block or blocks. The computer program instructions may also be loaded onto a computer or other programmable apparatus to cause a series of operational steps to be performed in the computer or on the other programmable apparatus to produce a computer implemented process such that the instructions that execute on the computer or other programmable apparatus provide steps for implementing the functions specified in the flowchart block or blocks.

Accordingly, blocks of the flowchart illustrations support combinations of means for performing the specified functions and combinations of steps for performing the specified functions. It will also be understood that each block of the flowchart illustrations, and combinations of blocks in the flowchart illustrations, can be implemented by special purpose hardware-based computer systems that perform the specified functions or steps, or combinations of special purpose hardware and computer instructions.

Some portions of this specification are presented in terms of algorithms or symbolic representations of operations. These operations may include data stored as bits or binary digital signals within a machine memory (e.g., a computer memory). These algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve the manipulation of information elements. Typically, but not necessarily, such elements may take the form of electrical, magnetic, or optical signals capable of being stored, accessed, transferred, combined, compared, or otherwise manipulated by a machine. It is convenient at times, principally for reasons of common usage, to refer to such signals using words such as "data," "content," "bits," "values," "elements," "symbols," "characters," "terms," "numbers," "numerals," "words", or the like. These specific words, however, are merely convenient labels and are to be associated with appropriate information elements.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in, but not limited to, at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Determination of patient treatment protocol compliance has long been a challenge. An optimal drug dosage protocol often relies on precise control of several environmental factors such when (and if) a patient administers the proper dosage. The apparent low efficacy of a particular drug may be attributed to many factors but often it can be attributed to poor adherence by the patient of administration protocols. For example a particular drug may be optimally administered 4 times daily with approximate 6-hour intervals between administrations. Yet it is not uncommon to find that a patient, having complained that the drug has been ineffective, has missed one or two administrations of the drug or that rather than a 6-hour interval between dosages, the intervals vary from 4 to 8 hours.

One means by which to increase patient compliance is through a system that automatically and temporally delivers prescribed medicine with minimal patient interaction. Such innovation is present in a bio-synchronous bioactive agent delivery device of the present invention.

One embodiment useful for bioactive agent delivery and according to the present invention includes an absorbent material pretreated or combined with a bioactive agent. The term "absorbent material" refers herein to a material having the capacity or tendency to absorb another substance. The term "bioactive agent" refers herein to a substance that has an effect on a living organism.

Bioactive agents (or combinations thereof) suitable for transdermal and similar drug delivery include but are not limited to hormonal contraceptives, pain relievers, antidepressants, stimulants for treating, for example, ADHD, biopharmaceuticals, active agents useful in treating chronic conditions, opioids, alprazolam, apomorphine, azelastine, alprostadil, buprenorphine, bupropion, clonidine, dexamethasone, dextroamphetamine, diclofenac, dihydrotestosterone, enalpril, estradiol, androgen/estradiol, estrodiol/progestin, testosterone/estradiol, ethinyl estradiol, fentanyl, flurbiprofen, glucagon-like peptide 1, glucagon-like peptide 2, granisetron, insulin, lidocaine, memantine, methylphenidate, methamphetamine, nitroglycerine, nicotine, norethisterone acetate (NETA), norelgestromine, oxybutynin, parathyroid hormone, pergolide, phenteramine, pramipexole, ramipril, ropinirole, rotigotine, scopolamine, selegiline, tecrine, testosterone, timolol, tolterodine, tulobuterol, and vaccines.

Conditions effectively treated with bioactive agents delivered transdermally include but are not limited to anxiety, allergies, depression, hypertension, nausea, diabetes, neuralogic pain, Alzheimer's disease, obesity, smoking cessation, urinary incontinence, Parkinson's disease, motion sickness, male hypogonadism and female sexual dysfunction.

In this embodiment of a bioactive agent delivery device a pretreated absorbent material is associated with a reservoir that includes a solution and a membrane permeable to the bioactive agent. The absorbent material pretreated with bioactive agent is interposed between the reservoir and the membrane. In response to a control signal generated by the device through an internal timing mechanism or remotely triggered, the solution is dispensed from the reservoir and is received by the absorbent material pretreated with bioactive agent. The solution facilitates transfer of the bioactive agent from the absorbent material to the membrane. The membrane is in contact with the epidermis of a host (a human or an animal). As the membrane is permeable to the bioactive agent, this compound diffuses through the membrane from the absorbent material and into the epidermis of the host. In this way, bioactive agent is transdermally administered to the host of the drug delivery system.

In one embodiment of the present innovation, a solution is actively dispensed from the reservoir by a delivery mechanism that comprises a mode of force. The mode of force can be pressure which, for example, includes but is not limited to compressed foam, one or more gas generating cells and the like. By applying pressure to the solution in the reservoir, the solution is dispensed from the reservoir through a valve operable to control the flow of the solution from the reservoir to the absorbent material pretreated with bioactive agent. In accordance with another embodiment of the present innovation, a pump functions as the delivery mechanism operable to dispense the solution from the reservoir to the absorbent material pretreated with bioactive agent.

As mentioned, a timing mechanism is communicatively coupled to the delivery mechanism and is operable to generate the control signal to dispense the solution from the reservoir to the absorbent material pretreated with bioactive agent. In one embodiment of the present innovation, the timing mechanism communicatively coupled to the delivery mechanism is configured to generate the control signal according to a programmed administration schedule. In other embodiments the control signal can be remotely delivered to the device to signal application of the solution to the permeable membrane. As an example, the drug delivery device can be coupled to a human and programmed to administer a compound during sleep. By using this system, the patient is appropriately dosed without having to be inconvenienced by waking up and personally administering the bioactive agent.

One feature of the present invention collects patient compliance data regarding use of a bioactive agent delivery system and to uses that compliance data as a basis for near real-time modifications of treatment protocols and, when necessary, to initiate non-pharmaceutical behavioral support. The bioactive agent deliver device of the present invention provides a means by which to deliver a pharmacological agent to the patient via transdermal interaction.

These delivery mechanisms can include but are not limited to iontophoresis, micro-needles, sonoporation, transdermal diffusion, dermal abrasion, control heat activated transdermal delivery or subcutaneous drug delivery. As one of reasonable skill in the relevant art will appreciate, iontophoresis is a physical process in which ions flow diffusively in a medium driven by an electric field. Iontophoresis is to be distinguished from the carriage of uncharged molecules by diffusive fluxes of other molecules, especially of solvent molecules, for example by electro-osmosis, that is to say by flux of uncharged solvent molecules carried as a cross-effect of iontophoresis. Iontophoresis is thus active transport of matter due to an electric field.

Another means by which to transport medicine transdermally employs micro-needles. Micro-needles use bio-compatible, medical grade polymeric microstructures to overcome the dermal barrier properties of the stratum corneum so as to deliver a wide range of biopharmaceutical therapeutics. Micro-needles can be employed as a patch or device containing a variety of microstructures that penetrate and deliver the medication.

Sonoporation, or cellular sonication, is another means by which to transdermally deliver medication. Sonoporation is the use of sound (typically ultrasonic frequencies) for modifying the permeability of the cell plasma membrane so as to allow therapeutic treatment. Sonoporation employs the acoustic cavitation of micro-bubbles to enhance delivery of larger molecules to a cell. Controlled heat activated transdermal delivery, as another deliver means, uses heat to enhance microcirculation and local perfusion and/or blood vessel permeability so as to facilitate drug transfer to the systemic circulatory system. Similarly, a subcutaneous injection can administer the drug into the subcutis, the layer of skin directly below the dermis and epidermis, collectively referred to as the cutis. Subcutaneous injections are highly effective in administering vaccines and medications such as insulin, morphine, diacetylmorphine and goserelin. Each of these technologies, and the like, provide a means by which to administer a pharmacological agent to a patient via the dermal layer and can be adapted for use with the optimized bisynchronous bioactive agent delivery system of the present invention.

A bioactive agent dosage (treatment) protocol for use with one or more embodiments of the present invention is developed based on a variety of parameters. For example, a physician or addiction cessation specialist may collect data with respect to physiological and psychological factors to help determine which drug should be used an its initial dosage amounts. These factors may include the patient's gender, age, length of additive behavior, the type of addiction or ailment being treated, and conditional factors such as the environment in which the patient works or lives, etc. As previously discussed imputing into the drug dosage protocols (also referred to herein as the bio-synchronous and/or temporal treatment protocol) individual biorhythms and temporal cycles enhances the efficacy of the bioactive agent delivery system of the present invention. Indeed the treatment protocol of the present invention includes bio-synchronous and temporal administration of pharmacological elements based on patient innately rhythmic biological processes and/or individual patient temporal patterns. These treatment protocols can take into account individual biorhythms, pharmacological and ailment temporal factors as well as individualized temporal cycles/schedules. Recall that biorhythms are rhythmic biological cycles that affect one's ability in various domains, such as mental, physical and emotional activity. According to one theory these cycles begin at birth and oscillate in a steady (sine wave) fashion throughout life. Sinusoidal behavior would be expected from chemical and hormonal secretion functions with their biofeedback activity with respect to chemical concentration. While still controversial there is evidence that individuals do experience cyclic tendencies. Similarly certain ailments are more prevalent during aspects of an individual's daily (or other time period) cycle. For example, heart ischemia resulting in angina can be caused by spasm of the coronary arteries. This is a rare condition called vasospastic angina (also known as Prinzmetal's angina) and is not associated with exertion. It is also well documented that the symptoms of ischemic heart disease are more common in the morning hours than at any other time of day. Yet an individuals "morning hours" vary based on several factors. One individual may regularly wake at 6:00 AM and retire at 10:00 PM. Another may find 9:00 AM the more likely time to arise and retire at 2:00 AM. And yet another may work evenings and find their "morning hours" begin at 1:00 PM and they retire at 5:00 AM. While there is evidence that humans are affected by the diurnal and nocturnal cycles, symptoms associated with medical conditions and ailments can be affected by an individual schedules. The treatment protocols of the present invention account for numerous temporal and cyclic factors affecting a patient's symptoms. The treatment protocol of the present invention for an individual suffering from a cold or from influenza, for example, may find that a pharmacological treatment is applied based on factors such as when that individual normal goes to bed, arises and goes to work, their age, their gender, certainly the type disease/virus if it can be identified, their mental state, and any other factor that can be used to make the treatment be as individually effective as possible. Thus the term bio-synchronous is used, herein, broadly to be inclusive of a plethora of temporal and biological factors.

As with any patient administered medication, compliance with a treatment protocol is critically important in the determination of the drugs efficacy and whether the treatment protocol should be modified. According to one embodiment of the present invention, the bioactive agent delivery device maintains a precise record of dosages and delivery times of the prescribed medication. This data can therefor be wirelessly reported to a health professional or medical specialist for analysis. In other embodiments, the data can be used to initiate automated responses and adjustments to the treatment protocol based on established treatment algorithms. Using collected compliance data a medical specialist can assess the effect of the drug on the patient's symptoms with confidence that the prescribed treatment protocol has been followed. Similarly, if a patient reports that the desired or anticipated effect of the treatment protocol has not occurred, the medical specialist can assess whether the drug as been administered according to the predefined protocol before altering the treatment protocol. If the compliance data matches the predefined treatment protocol the specialist can, if warranted, modify the dosages or other protocol factors. If however the compliance data provides evidenced that the treatment regime was not followed, the specialist can accordingly stress with the patient the need to follow the treatment procedures as closely as possible or suggest other treatment processes.

FIG. 1 provides a high level depiction of a system for optimized bio-synchronous bioactive agent delivery. As shown, a user 110 employs a bio-synchronous bioactive agent deliver system 120 to implement a predetermined drug dosing protocols. The bio-synchronous bioactive agent delivery system 120 is initiated based on input from the user 110 as directed by a medical specialist. For example the user (patient) may input data into the device information such as normal waking hours, work regimes, meal times, sleep schedule, etc. Based on that information the bio-synchronous bioactive agent delivery system 120 can using algorithmic dosing processes, administer a select drug within a predetermined temporal dosing schedule. Algorithmic dosing is based on data collected from the patient. In addition, a compliance unit 130, coupled to the bio-synchronous bioactive agent delivery system 120, can collect and report data with respect to administration of the prescribed dosage. Upon the user setting up and initiating the bio-synchronous bioactive agent delivery system 120 the compliance unit 130 is activated. Along with directing the bio-synchronous bioactive agent delivery system 120 to administer a dose of medicine to the patient at a bisynchronous time, the compliance unit records and, in other embodiments, reports compliant events. Event details such as the time of the administration, the amount of the dose, the point at which dosing was ceased, and other biometric factors can be collected, stored, and reported. Moreover the system can determine, in one embodiment, whether the user removed the device, a treatment was missed, or if treatment was interrupted. Other embodiments can further collect physiological data such as pulse, temperature and blood pressure to assist in assessing the impact of treatment protocol.

To aid in reporting of data, the compliance unit 130 can further include, in one embodiment, a wireless transceiver 150 and a processor 160 for local processing of the treatment protocols and for conveying compliance information to a remote administrator. In one version of the present invention the medical specialist administrating the treatment can be informed of noncompliance with the treatment protocol so as to make contact with the patient via text or phone regarding non-compliance of the treatment protocol. For example upon the system detecting that it cannot administer a scheduled dose of medicine the non-compliance unit 130 can report the transgression to an administrator who can contact the patient and, if necessary, offer behavioral support to re-initiate the treatment protocols. In other embodiments the collected data can be downloaded upon a patient's regular medical visit to assess the overall effect of the treatment program. In another embodiment of the present invention, non-compliance data can be used as an input to an algorithmic process by which automated emotional support is initiated. For example, a report of non-compliance can trigger an automated message to encourage the patient to re-initiate treatment or contact their healthcare provider.

Another innovation, according to the present invention, is the ability to collect individual psychological and physiological data with respect to the effect of a particular disease and use such information to individually optimize a drug treatment protocol. For example, in the case of nicotine addiction, a smoker's craving for a cigarette or a similar nicotine delivery device may peak at certain periods of time during the day. These peaks may vary in intensity and timing from one person to the next. Research has shown that many smokers have an intense craving for cigarettes early in the morning, at lunchtime, in the evening after dinner, and before retiring for sleep, but the exact timing of these cravings differs in each individual. One embodiment of the present invention enables the user, in this case a smoker, to easily document and report when the craving for a cigarette occurs and rate the intensity of the craving.

According to one embodiment of the present invention an applicator, or similar user interface, on a smart phone, tablet or computer can quickly log details with respect to the experienced symptom. Details such as the time of the recordation of the event can automatically be requested but the application, based on the treatment protocol, can present the patient with a short, but effective inquiry to gain important details with respect to the symptom. In the case of a craving for a cigarette the application can ask when the craving occurred, what was the intensity, did the patient smoke a cigarette, was the patient under stress, when was the last med, and the like. This information can then be used to optimize the treatment protocol.

Using a temporal log of such inputs, algorithms can in one embodiment, determine the best (optimal) dosage application of nicotine or other cessation type of drugs to facilitate an optimized smoking cessation protocol to be administered by the bisynchronous drug delivery system of the present invention. These protocols can be individualized not only for the particular pharmacology being used but also for the physiological and psychological profile of the user. Moreover, this information can be correlated with user compliance information to determine whether the cravings and established treatment protocols of the bio-synchronous bioactive agent delivery system 120 are properly optimized.

Dosage and compliance administration data can further include information about whether or not, as well as when, a patient has been administered a particular dosage of medication. The dosage data is confirmatory information and can, in one embodiment, only be generated when the bio-synchronous bioactive agent delivery system 120 makes contact with the user's skin 110 and administers the medication. Thus this type of compliance information is different (and more accurate and reliable) than self reported information or data that may be generated by a proxy. The present system does not rely on patient interaction or recordation of the event. Once initiated, the application of medication is recorded, and in one embodiment, reported to a centralized server or secondary device for analysis.

In addition to dosage administration data, additional data, as described earlier, may be obtained from the patient using an application on a smartphone or similar electronic device. Patient data may be obtained such as: physiological parameter data, e.g., as may be obtained using a sensing device, including biological and physiological sensors; lifestyle data, such as historical information about the patient (e.g., the patients activities on a given day, how the patient was feeling, etc.) as well as physiological data such as the patient's feelings of cravings or anxiety; activities of the patient (e.g., whether or not the patient expects to exercise, whether or not the patient is feeling well, etc.); and the like.

Compliance and ancillary data gained from the patient and drug delivery device is then evaluated to determine whether a change in the treatment protocol is warranted and if so, provide a recommendation based on that determination. The dosage administration data can also be assessed to identify whether, based on the information received from the patient, such as compliance data, physiological parameters and lifestyle data, any modification should be made to the therapeutic regimen and treatment protocols in order to optimize the therapeutic regimen for the patient in some way. For example, based on patient inputter and compliance data it may be determined that the treatment protocol needs to be shifted to temporarily so as to initiate medication earlier.

A health care practitioner may evaluate the data, e.g., manually or through use of any convenient decision tool that may include a database, algorithm, actionable interface (e.g., in the form of a graphical user interface (GUI)), outcome measure, etc. The health care professional or similar individual may then employ the resultant recommendation based on this step and if necessary communicate the determination to the patient and/or device directly. In one embodiment of the present invention communication of the change in dosage or temporal protocols can be communicated verbally while the bioactive agent delivery system can be modified remotely. Alternatively, the health care practitioner may inform the patient that no change in therapeutic regimen should be made and that the patient should continue to follow the therapeutic regimen as previously specified to the patient.

The modulation of the therapeutic regimen, when made, may take a variety of different formats. For example, the modulation may take the form of a change in a pharmaceutical dosage regimen, e.g., in the amounts of active agent taken and/or the different types of active agents taken or the duration of the treatment. The modulation may also take the form of a change in the activity of the bioactive agent delivery system. In addition, the modification may include lifestyle alteration recommendations, e.g., instructions to refrain from exercise, instructions to engage in exercise, instructions to modify diet, and the like. As mentioned, one feature of the present invention is the ability to wirelessly communicate with the bioactive agent application device so as to control the dosage and temporal delivery of a particular pharmacology. In one embodiment of the present invention the determination of the delivery protocol can be calculated and thereafter delivered to the delivery device wirelessly while in another embodiment the delivery device receives raw data from the data collection device and then formulates the revised delivery protocols locally. In alternative embodiments the protocols and the delivery mechanisms are determined and delivered on a distributive basis.

As mentioned, one or more embodiments of the present invention involves an application that would reside on a smartphone, laptop, PDA, or the like in which an individual's personal data is used to form a profile as the basis for determining dosage amounts and the timing thereof. For example information such as the gender of the individual, age, weight, and the like can be gathered in the formation of a profile and then used in conjunction with the cravings data to determine proper dosages, or the need of a bolus (a one time administration of medication), and when those dosages should be applied. Other disease specific information can also be gathered such as (for smoking cessation) how many cigarettes does the user normally smoke in a day, the type and strength of these cigarettes, does the user smoke when consuming alcohol, or coffee, and the like. The application can prompt the user to answer questions on topics ranging from the current emotional state, the urge to smoke at that moment in time, if they had smoked during the day or within a preceding period of time, smoking events, and/or other emotional or environmental factors that may contribute to their desire to smoke. Also the program can establish how motivated or driven the individual is with respect to smoking cessation. For example, the protocol for a heavy smoker that only wants to decrease the number of cigarettes he or she desires during the course of a day may differ from a light smoker may want to cease smoking altogether. Furthermore, another individual may want to quit smoking within a predetermined period of time, for example a month, while another smoker may want to gradually decrease the number of cigarettes they smoke each day over a period of six months to arrive smoke-free at some particular goal date. Each of these inputs affects the dosage and temporal application of the appropriate cessation drug based on a differing algorithm approach.

Figure 2:
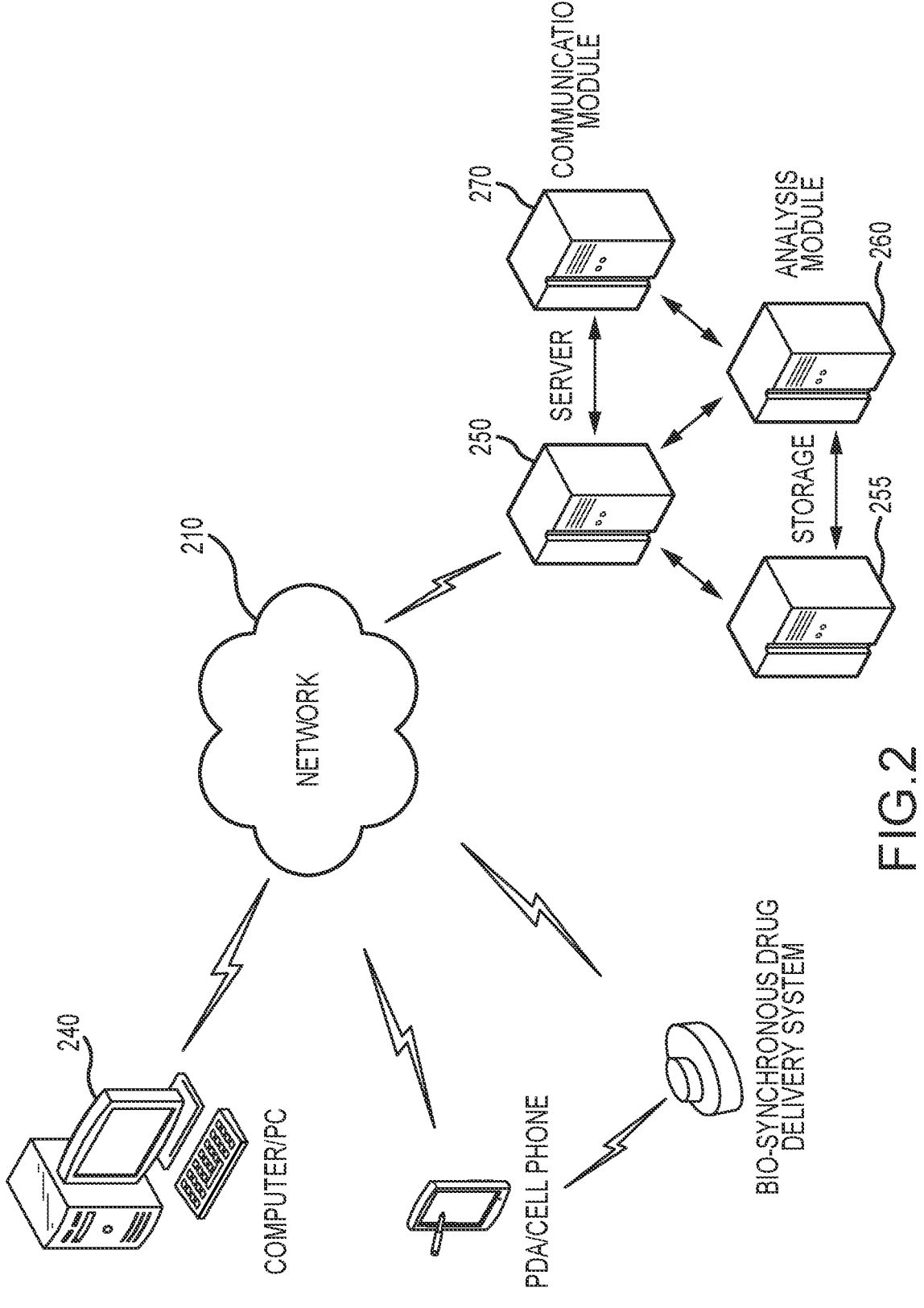
FIG. 2 depicts a network diagram suitable for the implementation of an optimized bio-synchronous bioactive agent delivery system according to one embodiment of the present invention.

FIG. 2 shows a high-level network environment in which a system for optimized bio-synchronous bioactive agent delivery can be implemented. As shown, the bio-synchronous bioactive agent delivery system of the present invention is, in one embodiment, communicatively coupled to a network 210 such as the Internet or an Intranet. A personal data assistant, smartphone, tablet or the like 230 can also collect and convey user information via the network 210, in addition to the bio-synchronous bioactive agent delivery system 220, to an analysis or administration server 250. The administrative server 250 can further possess storage devices 255 to memorialize and retain the data for further analysis. The administrative server 250 and storage device 255 can further be communicatively coupled to an analysis server 260 which can apply optimization and treatment algorithms to determine a suitable an optimized treatment protocol. This information can then be conveyed back the transdermal delivery device 270 via the network 210 to provide the patient with optimal treatment protocols. While a preferred embodiment envisions the use of mobile devices 230 as a means by which to collect user data including the occurrence and onset of a craving, the system is equally capably of gaining such information by a user's interface with a personal computer 240 or the like. Indeed the device 270 itself can be equipped with certain physiological sensors to record physical parameters of the user that may be later correlated with the efficacy of the treatment protocol and report these candidates to a central server.

While one embodiment of the present invention comprises a digital application resident and executable on a device such as a smart phone, PDA, cellular phone, or the like, one of reasonable skill in the relevant art will recognize that a separate data collection device can also be utilized to memorialize the applicable data and indeed be incorporated into the bio-synchronous drug delivery system of the present invention. Such a device, regardless of form, generally comprises a central processing unit(s) (CPU) or processor(s) coupled to a random-access memory (RAM), a read-only memory (ROM), a keyboard or user interface, and a display or video adapter connected to a display device. These devices may also optionally include a removable (mass) storage device (e.g., floppy disk, CD-ROM, CD-R, CD-RW, DVD, or the like), a fixed (mass) storage device (e.g., hard disk), a communication (COMM) port(s) or interface(s), a modem, and a network interface card (NIC) or controller (e.g., Ethernet, transceiver).

In such a system the CPU communicates with other components of the system via a bi-directional system bus (including any necessary input/output (I/O) controller circuitry and other "glue" logic). The bus, which includes address lines for addressing system memory, provides data transfer between and among the various components. Random-access memory serves as the working memory for the CPU. The read-only memory (ROM) contains the basic input/output system code (BIOS)—a set of low-level routines in the ROM that application programs and the operating systems can use to interact with the hardware, including reading characters from a user interface such as a keyboard, or outputting characters to printers, and so forth.

Mass storage devices provide persistent storage on fixed and removable media, such as magnetic, optical, or magnetic-optical storage systems, flash memory, or any other available mass storage technology. The mass storage may be shared on a network, or it may be a dedicated mass storage. The fixed storage typically stores a body of program and data for directing operation of the computer system, including an operating system, user application programs, driver and other support files, as well as other data files of all sorts. In basic operation, program logic (including that which implements methodology of the present invention) is loaded from the removable storage or fixed storage into the main (RAM) memory, for execution by a CPU. During operation of the program logic, the system accepts user input from various forms of a user interface such as touch screen or keyboard. In this manner, these input devices support manual user input for any process running on the system.

It is also contemplated that such a drug delivery system used in conjunction with the present invention can communicate with other devices (e.g., other computers, smart phone, PDA) wirelessly via a network interface card (NIC) connected to a network (e.g., Ethernet network, Bluetooth wireless network, or the like). The system may also communicate with local occasionally-connected devices (e.g., serial cable-linked devices) via the communication (COMM) interface, which may include a RS-232 serial port, a Universal Serial Bus (USB) interface, or the like. Devices that will be commonly connected locally to the interface include laptop computers, handheld organizers, smart phones and the like.

Regardless of the form of the device, the processors or internal processing capability will be capable of executing instructions embodied as software to collect, synthesize, and manipulate data so as to produce an optimal dosage protocol that can be transferred to, or by, a bioactive agent application device and to collect and convey compliance data regarding such treatment. The software programming code may be embodied on any of a variety of known media for use with a data processing system. It also may be distributed on such media, or may be distributed from the memory or storage of one computer system over a network of some type to other computer systems for use by such other systems. Alternatively, the programming code may be embodied in the memory of the device and accessed by a microprocessor using an internal bus or embodied as firmware or a combination of firmware and software. The processes embodied as software generally comprise program modules that include routines, objects, components, data structures and the like that perform particular tasks or implement particular abstract data types. The techniques and methods for embodying software programming code in memory, on physical media, and/or distributing software code via networks are well known and will not be further discussed herein. One key aspect of the present invention is the ability to provide near real-time emotional or psychological support to a user in conjunction with the use of the bio-synchronous bioactive agent delivery system. Support groups provide emotional counseling to assist patients during periods of intense emotional distress. Emotional support can be provided in the form of a phone call, voice mail, text message, email or the like. According to one embodiment of the present invention the bioactive agent delivery system can integrate one or more support features by which a user can gain emotional support. For example, upon experiencing an intense craving for nicotine the patient can communicate the experience to a counselor via a user interface associated with the present invention. As the system or the present invention works to provide the patient with emotional support it can also determine, based on the user profile and collected compliance data, whether an immediate bolus of additional medication is warranted. If so, the counselor or medical practitioner can remotely initiate the application of additional medication as emotional support is being administered. Similarly emotional support can be immediately offered without additional medication.

In other embodiments, the temporal application of medication through the bioactive agent delivery system can be supplemented by the presentation of proactive supportive emails, texts and the like. For example a user implementing the bioactive agent delivery system of the present invention that normally experiences a craving to smoke in the morning after awakening will receive medication to relieve that desire shortly before arising. Supplementing the medication can be a proactive text, email or phone call to further support the patient's non-use of the addictive substance.

Figure 3A:
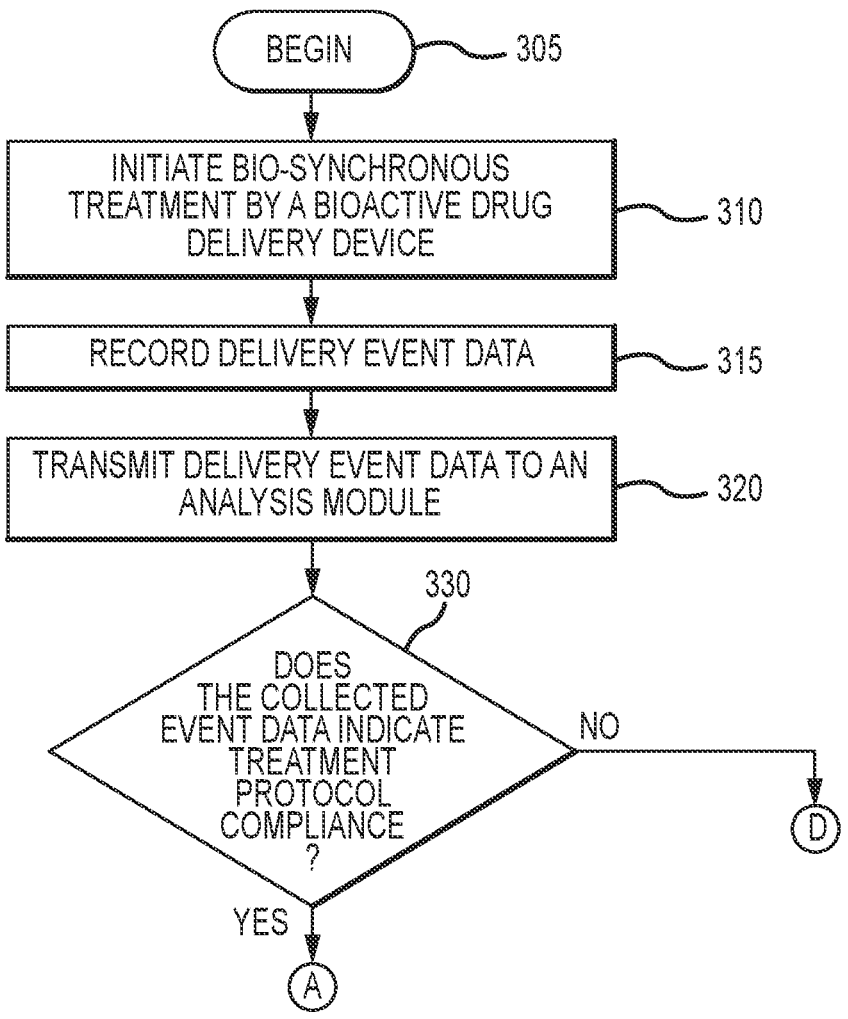
FIGS. 3A and 3B, correctively
Figure 3B:
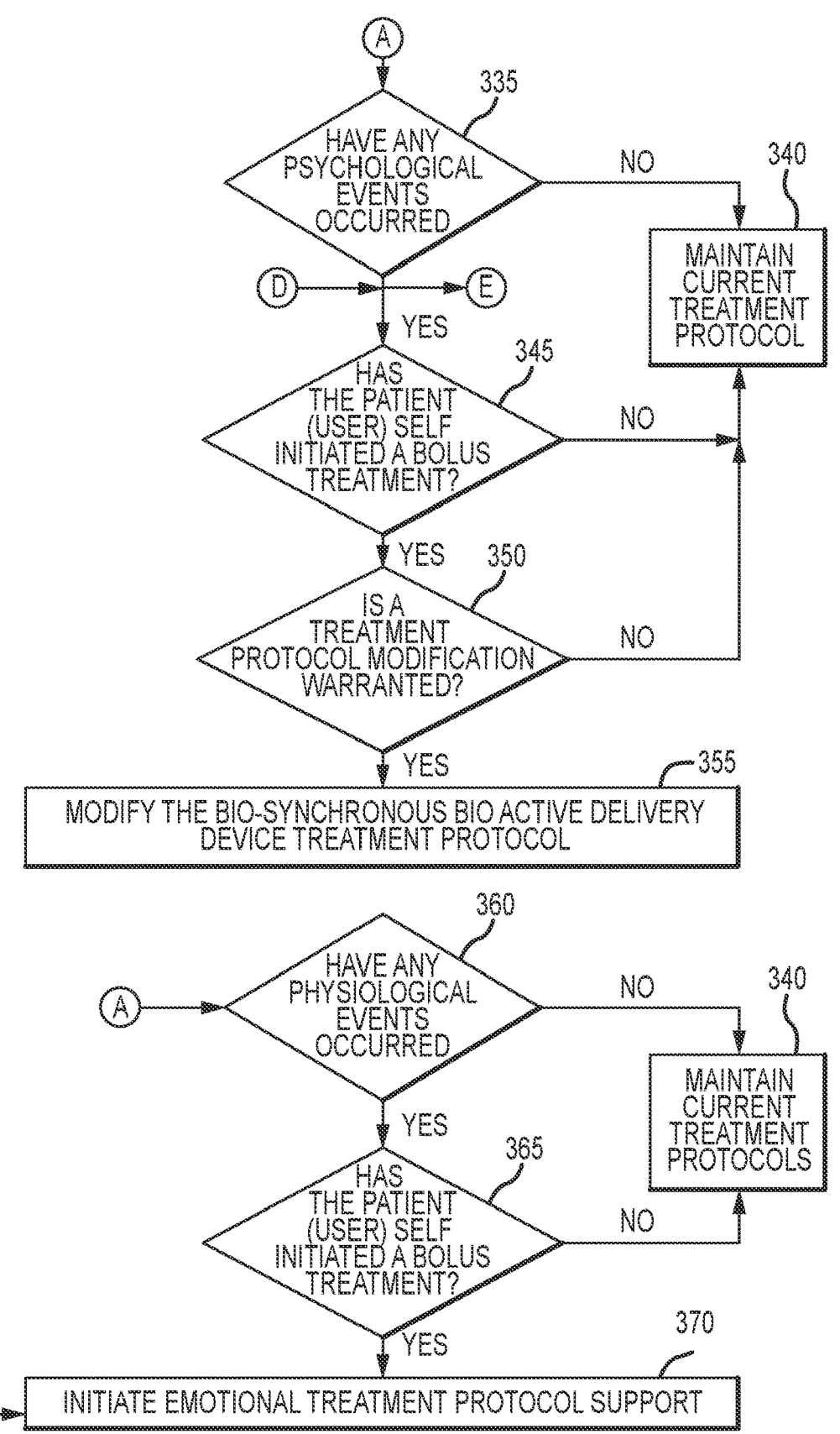

FIG. 3 is a high level flowchart of a methodology by which a bio-synchronous bioactive agent delivery device of the present invention can collect data with respect to treatment protocol compliance as well as psychological and physiological factors and apply a suitable treatment protocol. Such an exemplary process begins 305 with the initiation 310 of a bio-synchronous transdermal treatment protocol using a bioactive agent delivery device. Initially the bioactive agent delivery device is programed to deliver predetermined dosages of a particular drug according to a temporal plan as determined by an attending physician or clinical expert. These predetermined treatments may be formed by a user responding to a series of inquires to determine the scope of the treatment and its initial temporal application. For example, the physician may gain information with respect to the patient's physical attributes such as the patient's age, gender and weight as well as historical data with respect to the particular illness being treated. Environmental factors can be considered as can the patient's typical schedule. A wide variety of information can be gained to enable the physician through use of one or more algorithms to determine an initial, and later optimal treatment protocol. Once determined that initial treatment protocol can be programed into the transdermal treatment device and initiated by the user aid then later optimized by using newly gained information.

Once the treatment protocol is initiated 310 the bioactive agent delivery device not only applies the appropriate dosages at the predetermined intervals but records data associated with each treatment event 315. For example, in one embodiment, the device of the present invention can sense its proximity to a user's epidermis and upon application of the treatment record and report successful compliance with the treatment protocol. Similarly, if the device is no longer in contact with the user's epidermis and the treatment protocol indicates a dosage is due, the device can record a non-compliant treatment protocol event.

These recorded events can, along with additional information, be transmitted 320 to a data analysis module for further consideration. In one embodiment the bioactive agent delivery device possesses a wireless transmitter that can directly interact with a network environment such as the Internet to affect such transference of data. In other embodiments, the bioactive agent deliver device can wirelessly (or serially) couple with a cell phone, PDA or the like via Bluetooth or similar short range wireless data connection technology to convey the data which can then be processed locally or relayed to an analysis module for consideration.

Once the data is collected and reported the analysis module, in one embodiment of the present invention, can determine whether the collected event data indicates treatment protocol compliance 330. When the inquiry as to compliance indicates that the patient has followed the initial treatment protocols the system may further seek to determine whether any psychological events correlate 335 with the applications of the prescribed treatments. Psychological events can include such things as the recordation of an intense craving or similar symptom. Thus despite the patient's compliance with the treatment protocol, the patient's report of an ongoing problem may indicate evidence of an ineffectual treatment protocol. Conversely, the lack of any emotional events correlated with compliance with the treatment protocols may enable the system to conclude that the current treatment protocol should be maintained 340.

One additional aspect of the bio-synchronous bioactive agent delivery device of the present invention is the ability to self-administer a bolus 345 of a particular treatment drug. For example, a drug reservoir of the bioactive agent delivery device may possess sufficient capacity that even with full compliance with the prescribed treatment protocols a reserve of the prescribed drug is present to enable the user to safely prescribe a one-time bolus. The present invention records such an event and correlates it with both compliance data and any psychological inputs to address the efficacy of the treatment protocol. Thus even if the patient reported an intense craving but nonetheless did not avail themself to a bolus, the system may elect to maintain 340 the current protocol of treatments.

However, when data indicates that the patient has complied 330 with the predetermined treatment protocols, and registered a psychological event 350 such as an intense craving and self-initiated 345 a bolus of the prescribed drug, an inquiry may be begun 350 as to whether the treatment protocol should be modified.

Using collected data, the analysis module determines whether the existing treatment protocol should be modified. While the analysis may determine that the current protocol is to be maintained 340 the present invention, based on collected data, may move to modify 355 the current treatment protocol to increase the patient's opportunity for success. Modifications can include adjusting the temporal application of the drug, modifying the amount of dosage and even modifying the type of drug. For example, the system may determine that the current application of a particular dose should occur 30 minutes earlier to counter the patient's registration of an intense craving to smoke early in the morning. After applying the modification to the device and continuing to collect data the system may once again modify the protocol but this time increase the dosage of the prescribed drug. These modifications can be predetermined, directed by a health care provider, automated or any combination thereof so as to arrive at an optimized treatment protocol.

The methodology shown in FIG. 3 can also report that the patient has been non-complaint with the prescribed treatment protocol. Again the system can determine whether the patient has recorded a psychological event 360 such as a craving or whether the user has initiated a bolos treatment 365.

Using this information the analysis module can again determine whether a modification 345 to the treatment protocol is warranted. In one embodiment of the present invention the response to a non-compliance of the prescribed treatment protocol can be to maintain the protocol and to encourage compliance by offering emotional support 370. Similarly if the patient self-initiated a bolus 365 the system can use the information an additional application of the treatment drug (although non-complaint) to determine whether the treatment protocol should be modified 350.

The process shown in FIG. 3 further indicates, according to one embodiment of the present invention, the ability to combine physiological support for the treatment of an ailment with pharmacology (via the bio-synchronous bioactive agent delivery device) with psychological/emotional support. The initiation of 370 emotional treatment protocol support can be triggered by multiple events, and in other embodiments be proactively initiated to hopefully prevent the occurrence of non-compliance or a psychological event.

For example, upon a user indicating that a craving is occurring, the present invention can record the psychological event for use in determination of whether the treatment protocols should be modified, as well as initiate emotional support to assist the user in overcoming the challenge. A patient may find, despite compliance with the treatment protocol that a continuing craving is occurring. While the system may modify the protocol for future treatments, immediate support can be conveyed to the patient to remain compliant with the plan, and in the case of smoking cessation treatment, not smoke or, if necessary, to administer a bolus of the prescribed drug to assist in not smoking.

Likewise, a report of non-compliance can trigger emotional support in the form of a message to encourage the patient to comply with the treatment protocol or directly interact with support personal. For example, these reports can in one embodiment, be automated, while in other embodiments of the present invention, involve the interaction of a healthcare provider or a support group so as to provide individualized and personal contact with the patient.

One of reasonable skill in the applicable art will recognize that the present invention is especially adept to assist the treatment of addiction. Indeed one contemplated application of the innovations of the present invention includes the treatment for cessation of nicotine addiction. Prior approaches regarding nicotine replacement therapies include a variety of protocols and treatment regimens to aid the user in smoking cessation. Many of the decision trees or adaptive treatment strategies clarify decision rules, indicate how to integrate different treatment regimens, and provide recommendations on how to use or apply various nicotine replacement drugs. However, none of the prior art regiments or protocols provides any integration, or optimization for an individual patient, or the inclusion of emotional support. In many cases, an attending physician provides such optimization or treatment suggestions, but these suggestions or recommendation are not timely applied. One embodiment of the present invention is to utilize collected data, and user profile information to establish pharmacology and addiction cessation treatment regimens that implement an optimal drug delivery protocol to the bioactive agent delivery device that can be modified on a near real-time basis, with additional emotional support.

One feature of the present invention is the ability to continually monitor, modify and optimize the treatment regimen. As one of reasonable skill in the relevant art will appreciate, there are numerous smoking cessation protocols available to clinicians and physicians to aid in the development of a smoking (or addictive drug) cessation program. According to one embodiment of the present invention, a system is implemented to collect data regarding addictive cravings as well as other information such as compliance that can be used to determine an appropriate integrated and optimized treatment regimen. While individual data regarding the user's is an important aspect in determining the correct dosage of cessation assisting drugs, other information with respect to each individual must and can be gathered and applied to arrive at an optimal dosage delivery program. The present invention not only collects data with respect to the time, duration, and intensity of craving but also information with respect to the individual state of mind, and environmental factors that may have significant impact on the success of the drug delivery protocol.

The present invention thus collects a wide variety and range of data from an actual smoker or disease sufferer and determines and implements an optimal drug delivery protocol. This optimal drug delivery protocol can thereafter be transferred, either wirelessly or serially, to a bioactive agent delivery device. Included in this calculation is this determination, for this particular user, what the optimal transdermal flux rate and nicotine (drug) plasma concentration should be. By producing such information the bioactive agent delivery device can deliver to this user the optimal amount and temporal application of the appropriate drug.

Figure 4:
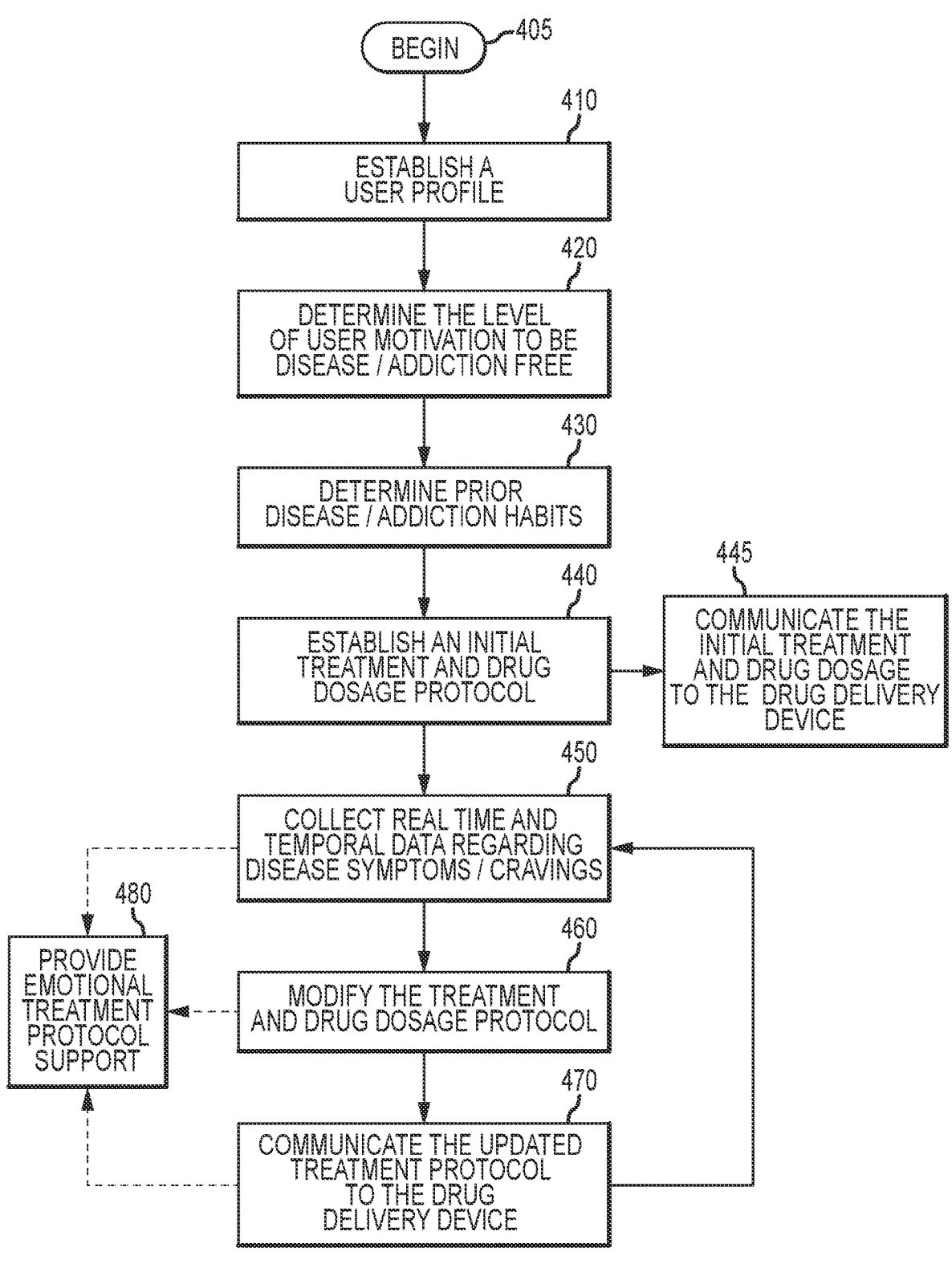
FIG. 4 is a high level flowchart of a method for determination of a bioactive agent delivery protocol and facilitating patient drug delivery compliance and cessation advocacy according to one embodiment of the present invention.

FIG. 4 is, according to one embodiment of the present invention, a high level flow chart of a methodology to determine and to optimize an addictive drug cessation program using a bioactive agent delivery device. The process begins 405 by establishing a user profile 410. The user profile, as discussed herein, includes various personal data with respect to the individualized user as well as historical addictive data. Once a user profile has been established the user can indicate 420 their level of motivation to be free of their symptoms or addictive tendencies. This combined with their prior symptoms/addictive habits 430 can establish an initial treatment protocol 440 that can be thereafter transmitted 4450 to the bioactive agent delivery device. Using this initial treatment protocol the bioactive agent delivery device can provide established and predetermined delivery of the cessation drugs to aid the user in terminating his or her addictive behavior. (Other classes of drugs can also be used based on the condition being treated.)

After the initial implementation, the system continues to collect 450 real-time temporal data regarding the user's symptoms or cravings and desires for the addictive item. For example with respect to smoking cessation, every time a smoker feels the need to have a cigarette the user can input that craving into the data collection application that can be used to validate or modify 460 existing cessation treatment protocols. Based on the data received from the user regarding their cravings and desires engaging and addictive behavior, the treatment protocol can be adjusted to provide either more or less cessation drugs as required. The new modified instructions or protocols can again be downloaded 470 to the bioactive agent delivery device for immediate implementation by the user. This process is iterative, STET continual and ends when the users is free for the symptoms of the disease i.e. the desire to smoke.

As the treatment protocol is being refined through the collection of data, the present invention can both proactively and reactively provide the patient with emotional treatment support 480. As a user indicates the existence of a craving or other symptom, the system can respond with a message via text or phone encouraging the user to maintain his or her conviction to the treatment protocol. Similarly, after recognizing that a patient is likely to experience a craving at a particular time of day, the system can proactively provide emotional support to once again maintain the program.

Figure 5:
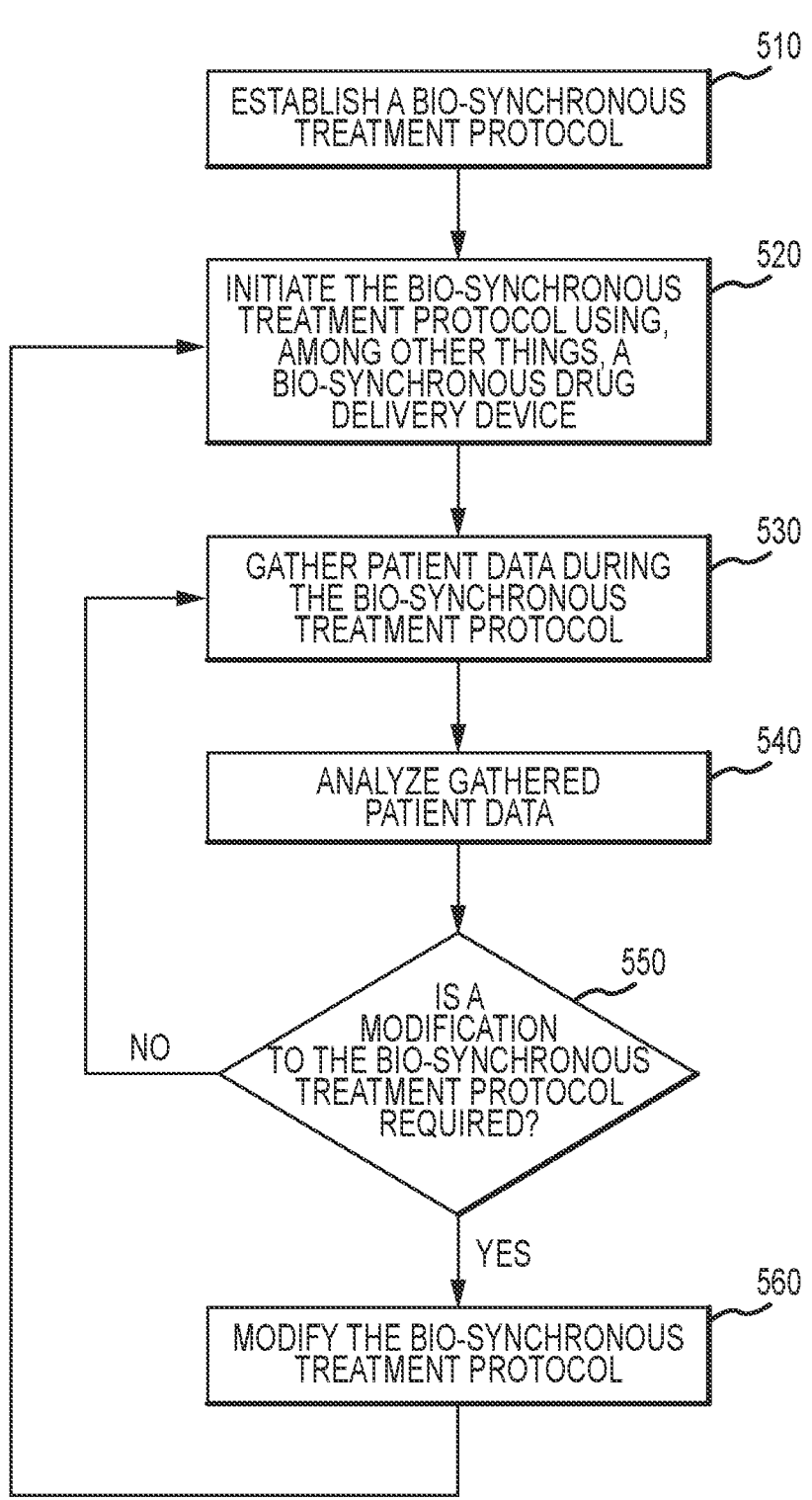
FIG. 5 is a high level flowchart of a method of optimized bio-synchronous bioactive agent delivery according to one embodiment of the present invention.

To better understand the novel features of the present invention consider the following example in view of FIG. 5. FIG. 5 presents one method embodiment for optimized bio-synchronous drug delivery. In accordance with the method shown in FIG. 5, assume an individual who has smoked consistently for several years wishes to stop smoking. That individual is a male, approximately 40 years old, weighs 190 pounds, and currently smokes on average one pack of cigarettes per day. This individual's current choice of cigarettes contains approximately 8 mg of nicotine per cigarette. This user typically smokes two cigarettes in the morning after arising at 6:00 AM, two or three cigarettes near or during lunch, and then two or three cigarettes after dinner (approximately 7:00 PM) before retiring for the evening. The individual has also indicated that he wishes to quit smoking within the next 30 days.

To ease this individual's desire for a cigarette he has elected to use a bioactive agent delivery device which can automatically provide a certain amount of nicotine at certain times throughout the day. In addition, and according to one embodiment of the present invention, this bioactive agent delivery device is linked to the system embodied as the present invention that optimizes the drug delivery protocol based on his individual characteristics, temporal environment, history, and desire to quit smoking.

After inputting the initial data into the system the drug delivery optimization system identifies and establishes 510 a specific protocol and drug cessation program that would most likely result in his cessation of smoking within 30 days. This protocol is uploaded to the bioactive agent delivery device so as to provide nicotine or other smoking cessation drugs at key points throughout the day, and to aid in his ability to resist the temptation to smoke. The program is initiated 520. As he wears the drug delivery device he interacts with the drug delivery optimization application to key in data with respect to cravings or desires to smoke a cigarette. As data is collected 530, and is processed (analyzed) 540, a new optimize drug delivery protocol is developed and delivered to the device. Additionally, the individual receives a combination of emails, texts, and voicemails encouraging his continued compliance with the program. These emotionally supportive messages may be proactive, reactive, or both. New (modified) drug delivery protocols are compared 550 to the existing drug delivery protocol currently in place in the bioactive agent delivery device. When the new drug delivery protocol substantively differs from the existing protocol the bioactive agent delivery device is updated 560 so as to provide the user with an improved and ideally optimal delivery of cessation aiding drugs.

For example, assume that every morning as the individual arises he has a strong desire to smoke a cigarette. The initial application of drugs has not effectively curtailed that desire. Therefore, immediately upon waking up the individual accesses the drug delivery optimization program on his smart phone or PDA and indicates his strong desire to have a cigarette. He may self-initiate a bolus of nicotine to overcome the desire to smoke. If he indeed does have a cigarette that data is inputted as well. Along with a measure of intensity of the desire, the program collects data with respect to when this particular craving occurred and correlates this event with other events in the past. If over a certain period of time the user consistently craves a cigarette between 7 AM and 7:30 AM, the application can modify the drug delivery protocol to provide increased nicotine supplements at an appointed time prior to 7 AM so as to prevent the craving. Moreover, at approximately 7:00 AM the user will receive an automated message encouraging him not to smoke. Similarly, if the user indicates that in the evening after a large meal he has no desire to smoke a cigarette yet after having a drink on Friday the craving returns, the drug delivery optimization program may determine that on Fridays from 4 to 6 PM a supplemental delivery of nicotine may be required to prevent a smoking event. In this manner the historical data input by the user is analyzed and used to optimize the dosage and delivery time of the transdermal drug.

In other embodiments of the present invention, the bioactive agent delivery device itself can be used to collect data and to modify its own programing while in other embodiments these modifications are determined remotely.

As will be understood by those familiar with the art, the invention may be embodied in other specific forms without departing from the spirit or essential characteristics thereof. Likewise, the particular naming and division of the modules, managers, functions, systems, engines, layers, features, attributes, methodologies, and other aspects are not mandatory or significant, and the mechanisms that implement the invention or its features may have different names, divisions, and/or formats. Furthermore, as will be apparent to one of ordinary skill in the relevant art, the modules, managers, functions, systems, engines, layers, features, attributes, methodologies, and other aspects of the invention can be implemented as software, hardware, firmware, or any combination of the three. Of course, wherever a component of the present invention is implemented as software, the component can be implemented as a script, as a standalone program, as part of a larger program, as a plurality of separate scripts and/or programs, as a statically or dynamically linked library, as a kernel loadable module, as a device driver, and/or in every and any other way known now or in the future to those of skill in the art of computer programming. Additionally, the present invention is in no way limited to implementation in any specific programming language, or for any specific operating system or environment It is to be clearly understood that the foregoing description is made only by way of example and not as a limitation to the scope of the invention. Particularly, it is recognized that the teachings of the foregoing disclosure will suggest other modifications to those persons skilled in the relevant art. Such modifications may involve other features that are already known per se and which may be used instead of or in addition to features already described herein. Although claims have been formulated in this application to particular combinations of features, it should be understood that the scope of the disclosure herein also includes any novel feature or any novel combination of features disclosed either explicitly or implicitly or any generalization or modification thereof which would be apparent to persons skilled in the relevant art, whether or not such relates to the same invention as presently claimed in any claim and whether or not it mitigates any or all of the same technical problems as confronted by the present invention. The Applicant hereby reserves the right to formulate new claims to such features and/or combinations of such features during the prosecution of the present application or of any further application derived therefrom.

What is claimed is:

1. A method for using a trans-dermal bioactive agent delivery device for optimizing bio-synchronous drug delivery, the method comprising:

establishing a bio-synchronous treatment protocol comprising bioactive agent delivery and temporal psychological support;

initiating the bio-synchronous treatment protocol wherein the bio-synchronous treatment protocol includes use of a bio-synchronous bioactive agent delivery device;

gathering patient data during the bio-synchronous treatment protocol;

analyzing patient data gathered by the trans-dermal bioactive agent delivery device;

determining based on gathered patient data whether modification to the bio-synchronous treatment protocol is required; and responsive to determining whether modification to the bio-synchronous treatment protocol is required, modifying the bio-synchronous treatment protocol to a modified bio-synchronous treatment protocol; and using the trans-dermal bioactive agent delivery device to administer the modified bio-synchronous treatment protocol.

2. The method of claim 1, wherein the bio-synchronous treatment protocol is based on at least one of individual biorhythms, ailment temporal factors, and individual temporal cycles or schedules.

3. The method of claim 1, wherein the bio-synchronous treatment protocol includes temporal administration of pharmacological elements based on individual patient temporal patterns.

4. The method of claim 1, wherein the bio-synchronous treatment protocol includes temporal administration of pharmacological elements based on patient innately rhythmic biological processes.

5. The method of claim 1, wherein the bio-synchronous treatment protocol includes temporal administration of pharmacological elements based on a combination of individual patient temporal patterns and patient innately rhythmic biological processes.

6. The method of claim 1, wherein the temporal psychological support is linked to patient temporal patterns.

7. The method of claim 1, wherein the temporal psychological support is linked to patient innately rhythmic biological processes.

8. The method of claim 1, wherein gathering patient data during the bio-synchronous treatment protocol comprises gathering data related to compliance with the bio-synchronous treatment protocol.

9. The method of claim 1, wherein gathering patient data during the bio-synchronous treatment protocol comprises gathering patient physiological data.

10. The method of claim 9, wherein patient psychological data includes a patient reported emotion.

11. The method of claim 10, further comprising providing temporal psychological support in reaction to the patient reported emotion.

12. The method of claim 11, wherein the patient reported emotion is anxiety or a craving.

13. The method of claim 1, wherein modifying includes remotely adjusting the bio-synchronous treatment protocol associated with the bio-synchronous bioactive agent delivery device.

14. The method of claim 1, wherein modifying the bio-synchronous treatment protocol to a modified bio-synchronous treatment protocol comprises changing a time of administration of the bioactive agent.

15. The method of claim 1, wherein modifying the bio-synchronous treatment protocol to a modified bio-synchronous treatment protocol comprises changing a dosage of bioactive agent to be administered.

* * * * *